United States Patent
Rubinstein et al.

(10) Patent No.: US 9,487,586 B2
(45) Date of Patent: Nov. 8, 2016

(54) METHODS FOR CANCER MANAGEMENT TARGETING CO-029

(71) Applicants: Eric Rubinstein, Villejuif (FR); Céline Greco, Villejuif (FR); François Le Naour, Villejuif (FR); Claude Boucheix, Villejuif (FR)

(72) Inventors: Eric Rubinstein, Villejuif (FR); Céline Greco, Villejuif (FR); François Le Naour, Villejuif (FR); Claude Boucheix, Villejuif (FR)

(73) Assignees: Institut National de la Santé et de la Recherche Médicale (INSERM), Paris (FR); UNIVERSITE DE PARIS XI PARIS SUD, Paris (FR)

( * ) Notice: Subject to any disclaimer, the term of this patent is extended or adjusted under 35 U.S.C. 154(b) by 0 days.

(21) Appl. No.: 14/691,630

(22) Filed: Apr. 21, 2015

(65) Prior Publication Data

US 2015/0291691 A1 Oct. 15, 2015

Related U.S. Application Data

(62) Division of application No. 13/811,353, filed as application No. PCT/EP2011/062650 on Jul. 22, 2011, now Pat. No. 9,040,671.

(30) Foreign Application Priority Data

Jul. 23, 2010 (EP) .................................... 10305818
Aug. 9, 2010 (EP) .................................... 10305875

(51) Int. Cl.
| | |
|---|---|
| *A61K 39/395* | (2006.01) |
| *C07K 16/28* | (2006.01) |
| *C07K 16/30* | (2006.01) |
| *C12N 15/113* | (2010.01) |
| *G01N 33/574* | (2006.01) |
| *C12N 5/09* | (2010.01) |
| *A61K 39/00* | (2006.01) |

(52) U.S. Cl.
CPC ........... *C07K 16/28* (2013.01); *A61K 39/3955* (2013.01); *C07K 16/3046* (2013.01); *C12N 5/0693* (2013.01); *C12N 15/1138* (2013.01); *G01N 33/57407* (2013.01); *G01N 33/57492* (2013.01); *A61K 2039/505* (2013.01); *C07K 2317/73* (2013.01); *C07K 2317/76* (2013.01); *C12N 2310/14* (2013.01); *G01N 2800/52* (2013.01)

(58) Field of Classification Search
CPC ................ C07K 16/00–16/468; C07K 16/28; C07K 16/3046; A61K 2039/505; C12N 15/1138; C12N 2310/14
See application file for complete search history.

(56) References Cited

U.S. PATENT DOCUMENTS

| 7,897,730 B2 | 3/2011 | Yu |
| 9,040,671 B2 * | 5/2015 | Rubinstein ............. C07K 16/28 530/387.3 |

FOREIGN PATENT DOCUMENTS

| CN | 101497662 A | * | 8/2009 |
| CN | 101497662 B | | 7/2012 |

OTHER PUBLICATIONS

Sela et al., Hybridoma, 1989; 8(4):481-491.*
Kanetaka et al., J. Hepatol., 2010; 35:637-42.*
Zhou et al., Clin. Exp. Metastasis, 2008; 25:537-48.*
Chan and Carter, Nature Reviews Immunology, 2010; 10:301-316.*
Ailane et al., Frontiers Physiol., 2014; 5:1-9 (doi: 10.3389/fphys.2014.00364).*
Chen & Xie, Int'l J. Nanomedicine, 2012; 7:3971-80.*
Ozpolat et al., J. Internal Med. 2009; 267:44-53.*
Ogris & Wagner, Human Gene Therapy 2011; 22:799-807.*
Fujita et al., Int. J. Mol. Sci., 2015; 16:5254-5270.*
Strome et al., The Oncologist, 2007; 12:1084-95.*
Brand et al., Anticancer Res. 2006; 26:463-70.*
Greco et al., Cancer Res, Oct. 1, 2010; 70(19):7674-83.*
El Kharbili et al., Abstract No. C30, J Invest Dermatol., Oct. 2009; 129:2528.*
Gesierich et al., "Systemic induction of the angiogenesis switch by the tetraspanin D6.1A/CO-029", Cancer Research, Jul. 15, 2006, pp. 7083-7094, vol. 66, No. 14.
Claas et al., "Association Between the Rat Homologue of CO-029, a Metastasis-associated Tetraspanin Molecule and Consumption Coagulopathy", The Journal of Cell Biology, Apr. 6, 1998, pp. 267-280, vol. 141, No. 1, Rockefeller University Press.
Azorsa et al., "A general approach to the generation of monoclonal antibodies against members of the tetraspanin superfamily using recombinant GST fusion proteins", Journal of Immunological Methods, Oct. 29, 1999, pp. 35-48, vol. 229, No. 1-2, Elsevier Science Publishers.
Kharbili et al., "Gene expression profiles of human melanoma cells with different invasive potential reveal TSPAN 8 as a novel mediator of invasion", Journal of Investigative Dermatology, Oct. 2009, p. 2528, vol. 129, No. 10, Abstract.

(Continued)

*Primary Examiner* — Sheela J Huff
*Assistant Examiner* — Jessica H Roark
(74) *Attorney, Agent, or Firm* — Whitham, Curtis & Cook, P.C.

(57) ABSTRACT

The present disclosure relates to a Co-029 inhibitor for inhibiting the migration of cancer cells which express Co-029. The disclosure relates to a Co-029 inhibitor for the treatment of cancer and/or the prevention of cancer metastasis and pharmaceutical compositions comprising said inhibitor and provides Co-029 antibodies. The disclosure provides a method for predicting the response of a patient afflicted with or susceptible to be afflicted with cancer to a medical treatment with a Co-029 inhibitor, a method for diagnosing a cancer in a patient and a method for predicting the survival in a cancer patient.

12 Claims, 8 Drawing Sheets

(56) References Cited

OTHER PUBLICATIONS

Figure 1A:
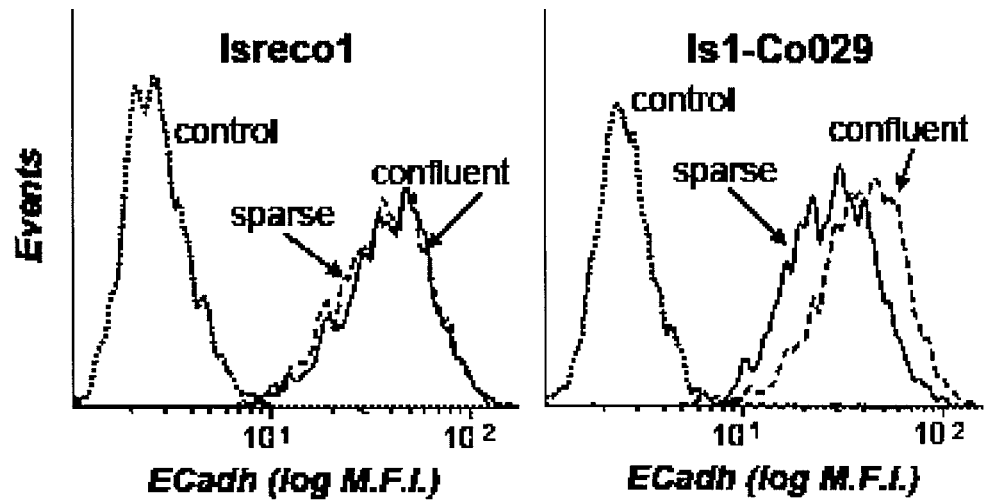
Figure 1B:
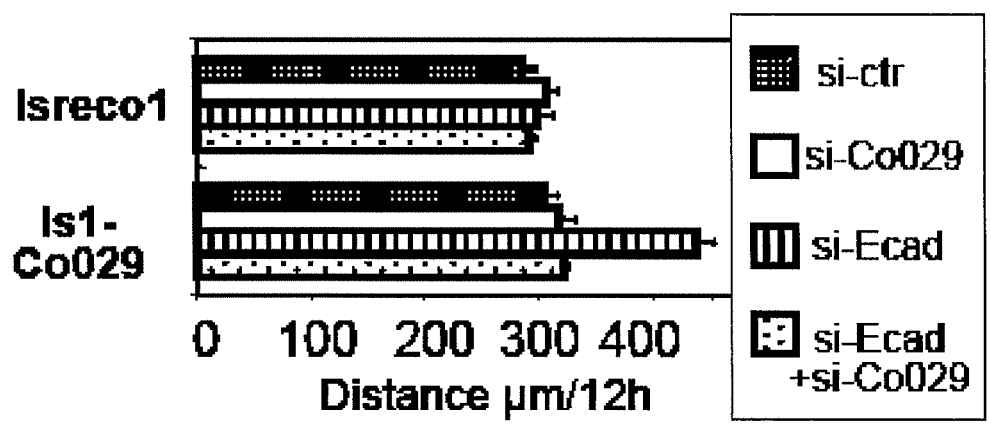

Jarikji et al., "The tetraspanin Tm4sf3 is localized to the ventral pancreas and regulates fusion of the dorsal and ventral pancreatic buds", Development, Jun. 2009, pp. 1791-1800, vol. 136, No. 11, Cambridge, GB.

Kanetaka et al., "Overexpression of tetraspanin CO-029 in hepatocellular carcinoma", Journal of Hepatology, Nov. 2001, pp. 637-642, vol. 35, No. 5.

Kuhn et al., "A Complex of EpCAM, Claudin-7, CD44 Variant Isoforms, and Tetraspanins Promotes Colorectal Cancer Progression", Molecular Cancer Research, Jun. 2007, pp. 553-567, vol. 5, No. 6.

Zhou et al., "TM4SF3 promotes esophageal carcinoma metastasis via upregulating ADAM12m expression", Clinical & Experimental Metastasis, Mar. 26, 2008, pp. 537-548, vol. 25, No. 5, Kluwer Academic Publishers.

Zijlstra et al., "The Inhibition of Tumor Cell Intravasation and Subsequent Metastasis via Regulation of In Vivo Tumor Cell Motility by the Tetraspanin CD151", Cancer Cell, Mar. 1, 2008, pp. 221-234, vol. 13, No. 3, Cell Press, US.

Greco et al., "E-Cadherin/p120-Catenin and Tetraspanin Co-029 Cooperate for Cell Motility Control in Human Colon Carcinoma", Cancer Research, Oct. 1, 2010, pp. 7674-7683, vol. 70, No. 19.

Yang et al., "Urokinase-Type Plasminogen Activator and its Receptor in Colorectal Cancer: Independent Prognostic Factors of Metastasis and Cancer-Specific Survival and Potential Therapeutic Targets", International Journal of Cancer, Sep. 20, 2000, pp. 431-439, vol. 89, No. 5, John Wiley & Sons.

Bellovin et al., "Altered Localization of p120 Catenin During Epithelial to Mesenchymal Transition of Colon Carcinoma is Prognostic for Aggressive Disease", Cancer Research, Dec. 1, 2005, pp. 10938-10945, vol. 65, No. 23.

Kanetaka et al., "Possible involvement of tetraspanin CO-029 in hematogenous intrahepatic metastasis of liver cancer cells", Journal of Gastroenterology and Hepatology, Nov. 2003, pp. 1309-1314, vol. 18, No. 11.

Gesierich et al., "Systemic Induction of the Angiogenesis Switch by the Tetraspanin D6.1A/CO-029", Cancer Res, 2006, pp. 7083-7094, vol. 66, No. 14.

Almagro & Franson, Frontiers in Bioscience, "Humanization of antibodies", 2008, pp. 1619-1633, vol. 13.

Dall'Acqua et al., "Antibody humanization by framework shuffling", Methods, 2005, pp. 43-60, vol. 36.

De Genst et al., "Antibody repertoire development in camelids", Dev Comp Immunol, 2006, pp. 187-198, vol. 30.

* cited by examiner

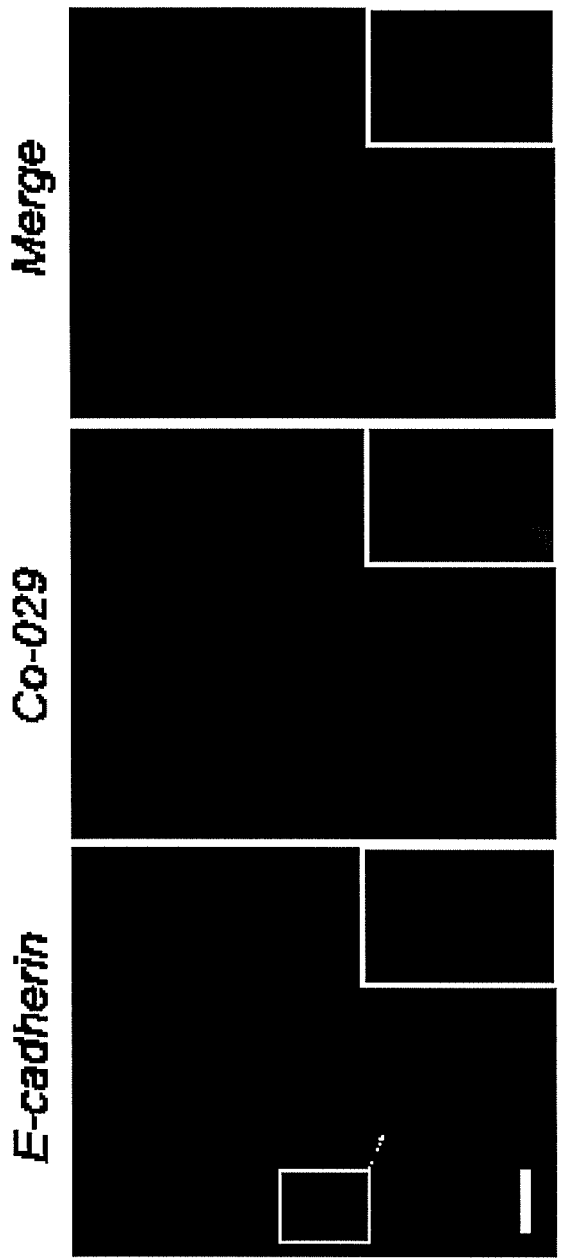
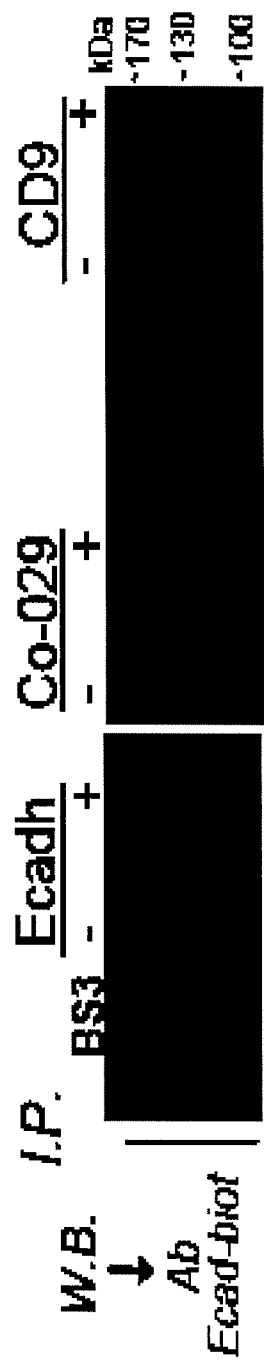
Figure 1C
Figure 1D

METHODS FOR CANCER MANAGEMENT TARGETING CO-029

FIELD OF THE INVENTION

The invention relates to methods for the treatment of cancer and/or the prevention of cancer metastasis. The invention also provides Co-029 antibodies and their use for the treatment of cancer and/or the prevention of cancer metastasis.

The invention further relates to diagnostic and predictive methods for cancer and/or cancer metastasis.

BACKGROUND OF THE INVENTION

Tetraspanins are a family of membrane glycoproteins found in all multicellular eukaryotes. Also called tetraspans or the transmembrane 4 superfamily (TM4SF), these proteins have four transmembrane domains, intracellular N and C-termini and two extracellular domains. Generally, tetraspanins are often thought to act as scaffolding proteins, anchoring multiple proteins to one area of the cell membrane. (Boucheix C. and Rubinstein E., 2001; Charrin, S. et al., 2009)

Tetraspanins are highly conserved between species. D6.1, the rat homologue of Co-029, present 74.2% homology in the nucleotide and a 70% homology in the amino acid sequence with Co-029 (Claas et al., 1998). Tetraspanins display numerous properties that indicate their physiological importance in cell adhesion, motility, activation and proliferation, as well as their contribution to pathological conditions such as metastasis.

Clinical studies have reported a link between tetraspanins and cancer and metastatic development. Particularly the level of expression of certain tetraspanins in a cancer is correlated with metastatic formation. More particularly, recent studies showed that the Co-029 tetraspanin expression is correlated with an increase of the metastasis potential in rat models of digestive tract tumors (Claas et al, 1998), in human liver (Kanetaka K. et al, 2003) and esophagus tumors (Zhou et al, 2008). More particularly, the inventors showed that the Co-029 tetraspanin was strongly expressed in metastatic cell lines of a colorectal carcinoma whereas it was absent on cells of the primary tumor (Le Naour, F. 2006). However there is no real demonstration of the direct role of Co-029 in metastatic development.

Immunohistochemical studies and transcriptional data suggest that in normal tissues and their malignant counterparts, the tetraspanin Co-029 is expressed mainly in the digestive tract including colorectal epithelium, oesophagus, liver and pancreas but it may also be found in prostate or trachea.

The restricted expression of Co-029 and its absence from circulating blood cells together with its expression on major tumor types with a relation to adverse prognosis suggest that it could be appropriately targeted for the treatment of cancer.

There is still a need for improving the management of treatment for cancer and cancer metastasis. Thus targeting the Co-029 pathway could be an interesting approach for therapeutic strategies in this domain.

SUMMARY OF THE INVENTION

The invention relates to Co-029 inhibitors for inhibiting the migration of cancer cells which express Co-029.

The invention relates to Co-029 inhibitors for the treatment of cancer and/or the prevention of cancer metastasis and pharmaceutical compositions comprising said inhibitors.

The invention relates to Co-029 antibodies and their uses for the treatment of cancer and/or the prevention of cancer metastasis.

The invention provides a method for predicting the response of a patient afflicted with or susceptible to be afflicted with cancer to a medical treatment with a Co-029 inhibitor comprising the following steps of:
- (i) determining the membrane levels of Co-029 and p120-catenin,
- (ii) comparing the membrane levels of Co-029 and p120-catenin obtained at step (i) with level obtained from levels obtained from reference sample,
- (iii) wherein an increased membrane level of Co-029 and a decreased membrane level of p120-catenin are indicative that said patient is a good responder to treatment.

The invention also provides a method for diagnosing a cancer in a patient, said method comprising the following steps of:
- (iv) detecting the membrane level of Co-029 in a biological sample obtained from said patient, and
- (v) comparing the membrane level of Co-029 in said biological sample to a level obtained from reference sample;
- (vi) wherein an increased membrane level of Co-029 than level obtained from reference sample is indicative of a bad prognosis cancer.

The invention further provides a method for predicting the survival in a cancer patient, said method comprising determining the membrane level of Co-029 in a biological sample obtained from said patient.

DETAILED DESCRIPTION OF THE INVENTION

Definitions

The term "Co-029" has its general meaning in the art and refers to a membrane protein of the family of tetraspanins also called TSPAN8 or TM4SF3 (Sela et al, 1989, Zoller, 2009, Charrin et al., 2009). The term may include naturally occurring Co-029 and variants and modified forms thereof. The Co-029 can be from any source, but typically is a mammalian (e.g., human and non-human primate) Co-029, particularly a human Co-029. An exemplary native Co-029 amino acid sequence is provided in GenPept database under accession number NP 004607 and an exemplary native nucleotide sequence encoding for Co-029 is provided in GenBank database under accession number NM 004616.

The term "p120-catenin" has its general meaning in the art and refers to a membrane protein of the family of catenins. The term may include naturally occurring p120-catenin and variants and modified forms thereof. The p120-catenin can be from any source, but typically is a mammalian (e.g., human and non-human primate) p120-catenin, particularly a human p120-catenin. An exemplary native p120-catenin amino acid sequence is provided in GenPept database under accession number AAH75795 and an exemplary native nucleotide sequence encoding for p120-catenin is provided in GenBank database under accession number NM_001085467.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The terms "cancer" or "neoplasms" include malignancies of the various organ systems, such as malignancies affecting lung, breast, thyroid, lymphoid tissues, gastrointestinal, and genito-urinary tracts, that include, but are not limited to, adenocarcinomas of the colon, prostate, lung and/or testicular tumors, non-small cell carcinoma of the lung, cancer of the small intestine and of the esophagus.

The term "cancer metastasis" has its general meaning in the art and refers to the spread of a tumor from one organ or part to another non-adjacent organ or part. Preferably, a cancer metastasis is more likely to occur when an increased level of Co-029 is observed in the primary tumor.

The expression "Co-029 inhibitor" should be understood broadly, it encompasses inhibitors of Co-029 expression and Co-029-specific binding molecules which are able to inhibit the migration of cancer cells which express Co-029.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA and maturation.

An "inhibitor of expression" refers to a natural or synthetic compound that reduces or suppresses the expression of a gene. Consequently an "inhibitor of gene expression" refers to a natural or synthetic compound that has a biological effect to inhibit or significantly reduce the expression of a gene.

An inhibitor of Co-029 expression refers to a natural or synthetic compound that reduces or suppresses the expression of a gene.

As used herein, the term "Co-029-specific binding molecule" is intended to refer to a molecule of sufficient size and complexity so as to be capable of selectively binding Co-029. According to the invention, such molecule is able to inhibit the migration of cancer cells which express Co-029.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody of the invention, and a CH domain and a CL domain of a human antibody.

According to the invention, the term "humanized antibody" refers to an antibody having variable region framework and constant regions from a human antibody but retains the CDRs of the antibody of the invention.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

The term "CO-029 antibody" refers to a monoclonal antibody directed against Co-029.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent (e.g., Co-029 antibodies) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The term "patient" refers to any subject (preferably human) afflicted with or susceptible to be afflicted with a cancer and/or a cancer metastasis.

In its broadest meaning, the term "preventing" or "prevention" refers to preventing the disease or condition from occurring in a subject which has not yet been diagnosed as having it.

In its broadest meaning, the terms "treating" or "treatment" refer to reversing, alleviating, inhibiting the progress of the disorder or condition to which such term applies, or one or more symptoms of such disorder or condition.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Therapeutic Methods and Uses

A first aspect of the invention relates to methods and compositions for the treatment of cancer and/or the prevention of cancer metastasis.

In one embodiment, the invention relates to Co-029 inhibitors for treatment of cancer and/or the prevention of cancer metastasis. Such inhibitor can be inhibitors of Co-029 expression or Co-029 specific binding molecules.

Inhibitors of Co-029 Expression

According to the invention, inhibitors of Co-029 gene expression, for use in the present invention, may be based on anti-sense oligonucleotide constructs. Anti-sense oligonucleotides, including anti-sense RNA molecules and anti-sense DNA molecules, would act to directly block the translation of Co-029 mRNA by binding thereto and thus preventing protein translation or increasing mRNA degradation, thus decreasing the level of Co-029, and thus activity, in a cell. For example, antisense oligonucleotides of at least about 15 bases and complementary to unique regions of the mRNA transcript sequence encoding Co-029 can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small interfering RNAs (siRNAs) can also function as inhibitors of Co-029 gene expression for use in the present invention. Co-029 gene expression can be reduced by introducing in cells from a subject a small double stranded RNA (dsRNA), or a vector or construct causing the production of a small double stranded RNA, such that Co-029 gene expression is specifically inhibited (i.e. RNA interference or RNAi). Methods for selecting an appropriate dsRNA or dsRNA-encoding vector are well known in the art for genes whose sequences are known (e.g. see Tuschl T et Al, 1999; Elbashir S M et Al, 2001; Hannon G J, 2002; McManus M T et Al, 2002; Brummelkamp T R et Al, 2002; U.S. Pat. Nos. 6,573,099 and 6,506,559; and International Patent Publication Nos. WO 01/36646, WO 99/32619, and WO 01/68836CD26CD26.

Examples of Co-029 siRNAs that could be used according to the invention include, but are not limited to, the three following stealth siRNAs available from Invitrogen: si-Co029s330, si-Co029s789, si-Co029s868. shRNAs (short hairpin RNA) can also function as inhibitors of Co-029 gene expression for use in the present invention.

Ribozymes can also function as inhibitors of Co-029 gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Co-029 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of Co-029 gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Co-029 Specific Binding Molecules

According to the invention, the Co-029 specific binding molecules are able to inhibit the migration of cancer cells which express Co-029.

In one embodiment, the Co-029 specific binding molecule may be a small organic molecule.

In another embodiment, the Co-029 specific binding molecule is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

In a certain embodiment, the Co-029 specific binding molecule is an antibody or antibody fragment that can partially or completely blocks the migration of cells which express Co-029 (i.e. a partial or complete Co-029 blocking antibody or antibody fragment).

In particular, the Co-029 specific binding molecule may consist in an antibody directed against the Co-029, in such a way that said antibody partially or completely blocks the migration of cells which express Co-029.

Antibodies directed against the Co-029 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against Co-029 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-Co-029, single chain antibodies. Co-029 inhibitors useful in practicing the present invention also include anti-Co-029 fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to Co-029.

Humanized anti-Co-029 antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In a preferred embodiment, said Co-029 specific binding molecule is a Co-029 antibody according to the invention.

In a certain embodiment, said Co-029 specific binding molecule is a Co-029 antibody obtainable from the hybridoma accessible under CNCM deposit number I-4046 or I-4047 or a Co-029 antibody which comprises the CDRs of antibody obtainable from the hybridoma accessible under CNCM deposit number I-4046 or I-4047.

In a particular embodiment, Co-029 specific binding molecule is a humanized antibody which comprises the CDRs of antibody obtainable from the hybridoma accessible under CNCM deposit number I-4046 or I-4047.

In another particular embodiment, Co-029 specific binding molecule is a Co-029 antibody fragment derived from antibody obtainable from the hybridoma accessible under CNCM deposit number I-4046 or I-4047.

The inventors have demonstrated that the antibodies of the invention are able to inhibit the cancer cell migration stimulated by Co-029. Thus, they can reduce cancer and metastatic progression.

The invention thus relates to a Co-029 antibody of the invention for the treatment of cancer and/or prevention of cancer metastasis.

The invention also relates to a method for treating and/or preventing a cancer metastasis which comprises the step of administering to a subject in need thereof an antibody of the invention.

In a particular embodiment, inhibitors and antibodies of the invention can be used for the treatment of cancer which express Co-029 and for the prevention of associated cancer metastases.

Examples of cancer metastasis which express or over express Co-029 and which could be treated with inhibitors and antibodies of the invention include but are not limited to metastatic colon, lung, pancreas, oesophagus and prostate cancers, melanomas and hepatocarcinomas.

The Co-029 inhibitor may be administered in the form of a pharmaceutical composition, as defined below.

Preferably, said inhibitor is administered in a therapeutically effective amount. By a "therapeutically effective amount" is meant a sufficient amount of the Co-029 inhibitor to treat and/or to prevent cancer metastasis at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

A further aspect of the invention relates to a pharmaceutical composition for treating and/or preventing cancer metastasis, said composition comprising a Co-029 inhibitor.

The Co-029 inhibitor may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of Co-029 of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of Co-029 of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Screening Methods

Inhibitors useful in the present invention may be further identified by screening methods which could be carried out according to known methods.

The screening method may measure the binding of a candidate compound to Co-029, or to cells or membranes bearing Co-029, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e g, inhibitor or substrate).

For example, Co-029 cDNA may be inserted into an expression vector that contains necessary elements for the transcription and translation of the inserted coding sequence. Following vector/host systems may be utilized such as Baculovirus/Sf9 Insect Cells Retrovirus/Mammalian cell lines like HepB3, LLC-PK1, MDCKII, CHO, HEK293 Expression vector/Mammalian cell lines like HepB3, LLC-PK1, MDCKII, CHO, HEK293. Such vectors may be then used to transfect cells so that said cells express recombinant Co-029 at their membrane. It is also possible to use cell lines expressing endogenous Co-029.

Antibodies of the Invention

The present invention provides for isolated antibodies or fragments thereof that are directed against human Co-029. In particular, the inventors have deposited two murine Co-029 antibody producing hybridomas at the Collection at the Collection Nationale de Cultures de Microorganismes (CNCM, Institut Pasteur, 25 rue du Docteur Roux, 75724 Paris Cedex 15, France), in accordance with the terms of Budapest Treaty, on the 18th of July 2008. The deposited hybridomas have CNCM deposit numbers CNCM I-4046 and CNCM I-4047.

A second aspect of the invention thus relates to a Co-029 antibody obtainable from the hybridoma available under CNCM deposit numbers CNCM I-4046 or CNCM I-4047.

The inventors have also cloned and characterized the variable domain of the light and heavy chains of said mAbTs29.2, and thus determined the complementarity determining regions (CDRs, according to IMGT unique numbering, Lefranc et al. (2009 Nucl. Acids Res 37: D1006-D1012) of said antibody (Table A).

TABLE A

Sequences of mAbTs29.2 domains.

| mAbTs29.2 domains | Sequence |
|---|---|
| VH | SEQ ID NO: 1: EVKVVESGGGLVQPGGSLRLSCATSGFTFTDYYMSWVRQ PPGKALEWLGFIRNRVSGYTTEYSASVQGRFTISRDNSQ SILYLQMNTLRAEDSATYYCARDHYGNFAMDYWGQGTSV TVSS |
| H-CDR1 | SEQ ID NO: 2: GFTFTDYY |
| H-CDR2 | SEQ ID NO: 3: IRNRVSGYTT |
| H-CDR3 | SEQ ID NO: 4: ARDHYGNFAMDY |
| VL | SEQ ID NO: 5: DIQMTQSSSSFSVSLGDRVTITCKASEDIYNRLAWYQQK PGNAPRLLISGATSLETGVPSRFSGSGSGKDYTLSITSL QTEDVASYYCQQYWSTPFTFGSGTKLEIK |
| L-CDR1 | SEQ ID NO: 6: EDIYNR |
| L-CDR2 | SEQ ID NO: 7: GAT |
| L-CDR3 | SEQ ID NO: 8: QQYWSTPFT |

In a particular embodiment, said antibody is selected from the group consisting of a murine antibody, a chimeric antibody, a humanized antibody, and a human antibody.

In another embodiment, the antibody of the invention comprise a variable light chain (VL) comprising the CDRs of the VL chain of the antibody obtainable from hybridoma deposited as CNCM I-4046 or CNCM I-4047 and a variable heavy chain (VH) comprising the CDRs of the VH chain of the antibody obtainable from hybridoma deposited as CNCM I-4046 or CNCM I-4047.

In another particular embodiment, the invention relates to a monoclonal antibody comprising a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3.

The invention also relates to a monoclonal antibody comprising a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

The monoclonal antibody of the invention, may comprise a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3 and a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

In particular, the invention provides an monoclonal antibody comprising an heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

In another embodiment, the antibody of the invention comprises the VL chain of the antibody obtainable from hybridoma deposited as CNCM I-4046 or CNCM I-4047 and the VH chain of the antibody obtainable from hybridoma deposited as CNCM I-4046 or CNCM I-4047.

In a particular embodiment, the heavy chain variable region of said antibody has the amino acid sequence set forth as SEQ ID NO: 1 and/or the light chain variable region has the amino acid sequence set forth as SEQ ID NO: 5.

In another embodiment, the antibody of the invention is a chimeric antibody, preferably a chimeric mouse/human antibody, which comprises the variable domains of the antibody obtainable from hybridomas deposited as CNCM I-4046 or CNCM I-4047. In particular, said mouse/human chimeric antibody may comprise the variable domains of mAbTs29.2 antibody as defined above.

In another embodiment, the antibody of the invention is a humanized antibody. In particular, in said humanized antibody, the variable domain comprises human acceptor frameworks regions, and optionally human constant domain where present, and the CDRs of the antibody obtainable from hybridoma deposited as CNCM I-4046 or CNCM I-4047, in particular, a non-human donor CDRs, such as mouse CDRs as defined above.

A further aspect of the invention thus relates to a murine monoclonal antibody (mAbTs29.2) obtainable from the hybridoma available under CNCM deposit number CNCM I-4047.

The invention further provides fragments directed against Co-029 of said antibody which include but are not limited to Fv, Fab, F(ab')2, Fab', dsFv, scFv, sc(Fv)2 and diabodies.

In another aspect, the invention relates to a polypeptide which has a sequence selected from the group consisting of SEQ ID NO: 1, SEQ ID NO:2, SEQ ID NO:3, SEQ ID NO:4, SEQ ID NO:5; SEQ ID NO: 6; SEQ ID NO:7 and SEQ ID NO:8.

A further aspect of the invention relates to a nucleic acid sequence encoding an antibody according to the invention.

In a particular embodiment, the invention relates to a nucleic acid sequence encoding the VH domain of the antibodies obtainable from hybridoma deposited as CNCM I-4046 or CNCM I-4047 or the VL domain of the antibodies obtainable from hybridoma deposited as CNCM I-4046 or CNCM I-4047.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further aspect of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further aspect of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a transformed host cell according to the invention under conditions suitable to allow expression of said antibody; and (ii) recovering the expressed antibody.

In another particular embodiment, the method comprises the steps of:

(i) culturing the hybridoma deposited as CNCM-I-4046 or CNCM-I-4047 under conditions suitable to allow expression of Co-029 antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human Co-029 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with human CO-029 with a protease, pepsin. Also, the F(ab')2 can be produced by binding Fab' described below via a thioether bond or a disulfide bond.

The Fab' of the present invention can be obtained treating F(ab')2 which specifically reacts with human CO-029 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation.

Depending on the coupling mode used, the sugar(s) may be attached to (a) arginine and histidine, (b) free carboxyl groups, (c) free sulfhydryl groups such as thoseof cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojar H T. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. No. 4,640,835; 4,496, 689; 4,301, 144; 4,670, 417; 4,791, 192 or U.S. Pat. No. 4,179,337.

Predictive Methods of the Invention

The third aspect of the invention relates to methods for predicting the metastatic potential of a cancer in a patient, predicting the survival in a cancer patient and predicting the response of a patient to a medical treatment.

For these three methods, membrane levels of biomarkers of the invention are assayed and compared with levels obtained from reference samples.

The term "biomarker" refers to a substance that is a distinctive indicator of a biological process, biological event, and/or pathologic condition. The biomarkers of the invention are proteins measured as indicators of cancer and/or cancer metastasis condition: Co-029 and p120-catenin.

According to the invention, the membrane levels of biomarkers are measured in a biological sample.

The term "biological sample" is used herein in its broadest sense. A biological sample is generally obtained from a patient. A sample may be of any biological tissue or fluid with which biomarker of the present invention may be assayed. Such samples include, but are not limited to, bodily fluids which may or may not contain cells, e.g., blood (e.g., whole blood, serum or plasma), urine, synovial fluid, saliva, and joint fluid; tissue or fine needle biopsy samples, such as from bone or cartilage, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

Typically, the biological sample used for studying a cancer according to the methods of the invention by assessing the membrane level of Co-029 and/or p120-catenin can result from a biopsy.

Level membrane of a biomarker of interest can be measured by techniques well known in the art.

The membrane portion of biological sample is extracted by centrifugation. After this first step, the level of said biomarker is measured in membrane extract by several methods well known in the art.

Such methods comprise contacting the membrane portion of biological sample with a binding partner capable of selectively interacting with membrane biomarker present in the sample. For determining the membrane level of biomarker, said binding partner has to bind extra-membrane region of said biomarker.

The binding partner is generally an antibody that may be polyclonal or monoclonal, preferably monoclonal.

In another embodiment, the binding partner may be an aptamer.

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays may involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The presence and the quantity of membrane biomarker can be detected using immunochemistry experimentations well known in the art.

The presence of said membrane biomarker can be detected using standard electrophoretic and immunodiagnostic techniques, including immunoassays such as competition, direct reaction, or sandwich type assays. Such assays include, but are not limited to, Western blots; agglutination tests; enzyme-labelled and mediated immunoassays, such as ELISAs; biotin/avidin type assays; radioimmunoassays; immunoelectrophoresis; immunoprecipitation, immunocytochemistry, immunohistochemistry, etc. The reactions generally include revealing labels such as fluorescent, chemiluminescent, radioactive, enzymatic labels or dye molecules, or other methods for detecting the formation of a complex between the antigen and the antibody or antibodies reacted therewith.

More particularly, an ELISA method can be used, wherein the wells of a microtiter plate are coated with a set of antibodies against the proteins to be tested. A biological sample containing or suspected of containing the marker protein is then added to the coated wells.

After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

After that, the membrane level of said biomarker assayed in a biological sample is compared with a levels obtained from reference samples.

The term "reference sample" refers to one or more than one sample that has been obtained from a healthy patient or tissue, or a patient who has been diagnosed with a specific disease other than cancer or a non cancerous tissue.

Preferably, the reference sample corresponds to the normal epithelial tissue adjacent to the tumor in a cancer patient.

Method for Predicting the Response of a Patient to a Treatment of the Invention

The invention describes strategy of treatment of cancer and/or prevention of cancer metastasis using Co-029 inhibitors.

The invention also provides a method for predicting the response of a patient afflicted with or susceptible to be afflicted with a cancer to a medical treatment with a Co-029 inhibitor comprising the following steps:
  (i) determining the membrane levels of Co-029 and p120-catenin,
  (ii) comparing the membrane levels of Co-029 and p120-catenin obtained at step (i) with level obtained from a reference sample,
  (iii) wherein an increased membrane level of Co-029 and a decreased membrane level of p120-catenin are indicative that said patient is a good responder to treatment.

The method above is based on the identification of particular levels of two prognostic biomarkers in cancer metastasis or cancer with predisposition of metastasis.

The membrane levels of p120-catenin and Co-029 are measured in a biological sample as explained above.

The membrane levels of p120-catenin and Co-029 are measured to evaluate the response to treatment with a Co-029 inhibitor.

A decreased membrane level of p120-catenin corresponds to a delocalisation to cytoplasm or/and a decrease of the expression of the protein. The delocalization of p120-catenin from the membrane is indicative of the presence of a metastasis or a high metastasis risk, and a poor prognosis.

Typically, the observation of a delocalization of p120-catenin to cytoplasm corresponds to a decreased membrane level of p120-catenin.

Such delocalization can be easily observed by immunohistochemistry.

An increased membrane level of Co-029 corresponds to a strong expression of the protein. This strong expression is indicative of the presence of a metastasis or a high metastasis risk, and a poor prognosis.

According to the invention, an increased membrane level of Co-029 refers to an equal or higher level than the level obtained from reference sample.

Treatment with a Co-029 inhibitor is considered to be more efficient in the case of a decreased membrane level of p120-catenin and an increased membrane level of Co-029.

The term "good responder to the treatment" refers to a patient who shows a reduction of cancer and/or cancer metastasis after said treatment.

The term "decreased membrane level of p120-catenin" refers to membrane level of p120-catenin equal or lower than a level obtained from reference sample.

The term "increased membrane level of Co-029" refers to membrane level of Co-029 equal or higher the level obtained from reference sample.

The present invention further provides kits suitable for determining the cancer metastasis of the invention.

Method for Predicting the Metastatic Potential of a Cancer in a Patient

The invention provides a method for diagnosing a cancer in a patient, said method comprising the following steps of:
  (i) detecting the membrane level of Co-029 in a biological sample obtained from said patient, and
  (ii) comparing the membrane level of Co-029 in said biological sample with level obtained from a reference sample;
  (iii) wherein an increased membrane level of Co-029 is indicative of high metastatic potential.

The membrane level of Co-029 can be measured as detailed above.

Method for Predicting the Survival in a Cancer Patient

The present invention relates to a method for predicting the survival of a cancer patient comprising determining the membrane level of Co-029 in a biological sample obtained from said patient.

Methods for determining the membrane level of Co-029 in a biological sample are detailed above.

Advantageously, the method of the invention further comprises a step of comparing the membrane level of Co-029 with a level obtained from reference sample. Said comparison is indicative of the survival for the cancer patient: an increased membrane level of Co-029 in the biological sample compared to the level obtained from reference sample associated with a shorter survival prognostic.

Another object of the invention is Co-029 as a biomarker of survival in cancer.

The method of the invention may be thus useful for classifying cancer patients and then may be used to choose the accurate treatment. For example, patients with a low score of survival may receive a more intensive treatment and attention compared to patient with a high score. Such method may thus help the physician to make a choice on a therapeutic treatment which can accordingly consist in administering accurate drugs to the patients.

Yet another object of the invention relates to a kit for predicting the survival of a cancer patient, comprising means for measuring the membrane level of Co-029 in a biological sample obtained from the patient. The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards.

FIGURES

FIG. 1A-D. Co-029 is functionally and physically linked to E-cadherin.

A, Surface expression of E-cadherin shows low variation of E-cadherin levels on sparse cells versus confluent cells. B, silencing of E-cadherin (si-Ecad) induces an increased motility restricted to Is1-Co029 cells and suppressed by co-silencing of Co-029 (si-Co029); averaged distance traveled by cells; error bars indicate s.e. C, Double labelling with anti-E-cadherin (biotin labelled rabbit polyclonal) and TS29 (mouse mAb to Co-029) antigen shows a partial colocalization at adherens junctions. (scale bar, 10 μm). D, The association of E-cadherin and Co-029 is suggested by experiments with the water-soluble cross-linker BS3. Each lane represents $\frac{1}{6}^{th}$ of two pooled 150 cm' flasks with confluent cells. Triton X100 extracts were immunoprecipitated (I.P.) by the mAb Hecd1 or by the Co-029 mAb TS29. Western blots (W.B.) performed with biotinylated antibodies revealed the presence of a band (arrowheads) above E-cadherin (arrow in the left upper panel) that could correspond to a Co-029/E-cadherin complex; (not cross-linked Co029 is also shown in the right lower panel (arrow)).

FIG. 2A-G. p120ctn regulates effects of Co-029 on cell motility.

A, the labelling of Is1-Co029 cells treated with control si-RNA (si-ctr) shows a colocalization of p120-catenin and E-cadherin at adherens junctions. Upon silencing by si-Ecad, E-cadherin has nearly disappeared (same exposure and contrast) whereas p120-catenin remains expressed but mainly concentrated around and over the nucleus area. A similar aspect was observed in both cell lines; scale bar, 20 μm. B, Is1-Co029 cells cultured on collagen I were detached and permeabilized for analysis of p120-catenin by flow cytometry 48 hours after p120ctn or E-cadherin silencing. The M.F.I. values are indicated below each conditions. This experiment shows that si-p120 reduces the amount of p120ctn by 80% whereas si-Ecad has no effect on p120-catenin expression. C, Surface E-cadherin of Is1-Co029 cells cultured on collagen I was analysed by flow cytometry after silencing by si-Ecad or si-p120. We observed a 75% and 50% reduction of surface E-cadherin upon, respectively, si-Ecad and si-p120 treatments, showing the requirement of p120ctn for E-Cadherin stability at the membrane. D-E, The motility of p120ctn silenced cells is increased when Co-029 is expressed. Gray lines represent cumulative distance traveled by individual cells versus time (D); the si-p120 effect on Is1-Co-029 cell motility is reversed by si-Co029; the x symbol indicates conditions that were not tested in this experiment. F, RNAi demonstrates a switch from α1 to α2 collagen receptor recruitment in Is1-Co029 cells, confirmed using function blocking antibodies. G, RNAi to α1 and α2 integrins shows that Is1-Co029 silenced for p120ctn can be slowed down by both si-RNA and cells treated with the three si-RNAs are stopped (NQ=Not Quantifiable); error bars indicate s.e.

Figure 3A:
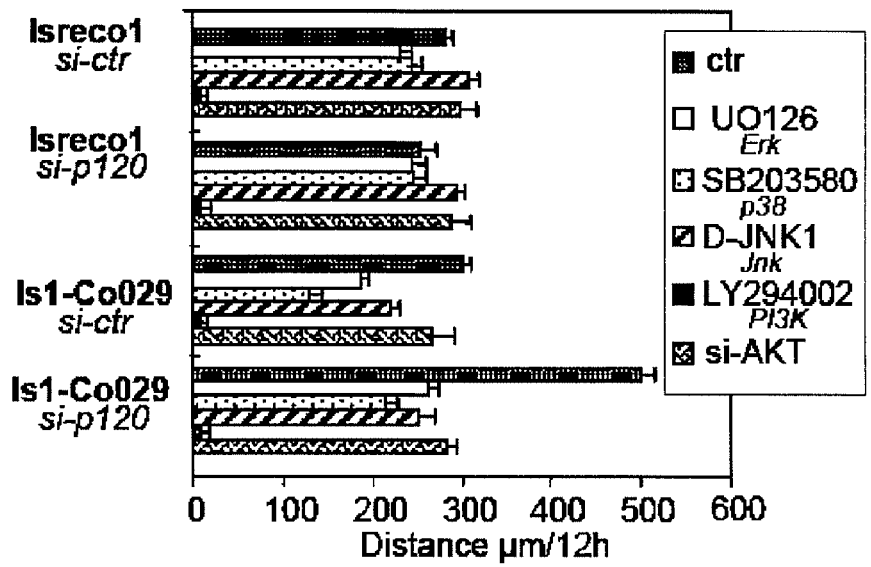
Figure 3B:
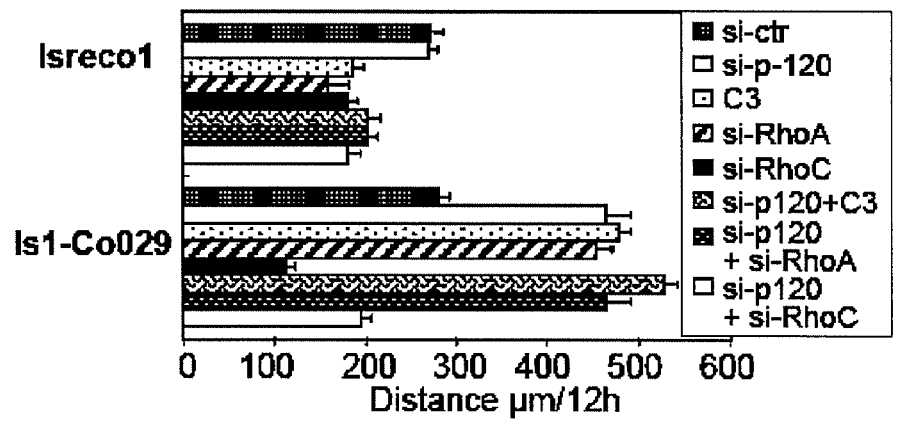
Figure 3C:
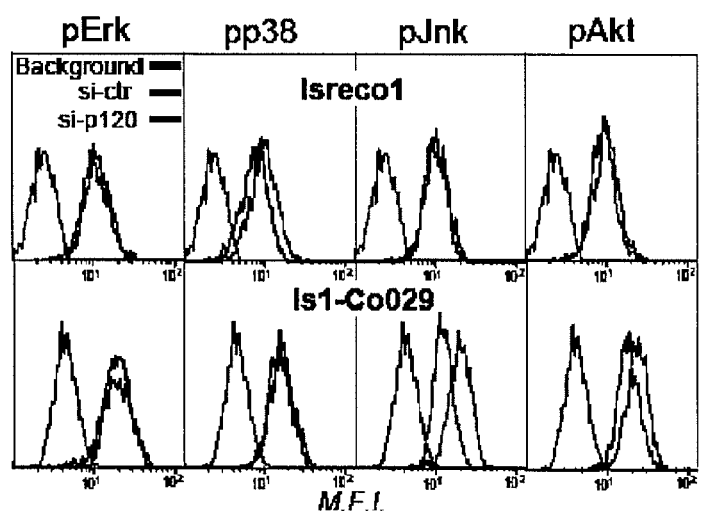
Figure 4A:
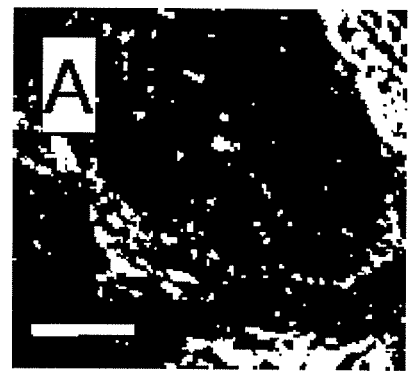
Figure 4B:
Figure 4C:
Figure 4D:
Figure 4E:
Figure 4F:

FIG. 3A-C. Multiple signalling pathways are triggered by Co-029 for cell motility.

A, The chemical MAPK inhibitors and si-Akt completely reversed the acceleration of Is1-Co029 cells induced by si-p120. B, C3 exotransferase (and si-RhoA) has the same effect on motility as p120-catenin silencing; it also induces the formation of a branching phenotype (Figure S6) that progressively blocks cell migration (motility was measured 12 to 24 hours after treatment). Since this effect is observed on both cell types, it is independent of the acceleration of cell motility observed in C3 treated Is1-Co029. C, The level of phosphorylated forms of signalling molecules was analysed by flow cytometry on sparse cells. The effect of si-p120 treatment on pAkt and pJnk was observed repeatedly for Is1-Co029 cells, whereas the variation of pp38 was not stable between different experiments.

FIG. 4A-F. Immunohistochemistry in human colon adenocarcinomas.

A, labelling of p120ctn on carcinomatous cells showing a membrane localization or (B) a delocalization to the cytoplasm. Higher intensity of Co-029 labe\lling of non tumorous colon epithelium (C) as compared to carcinomatous cells (D) in the same patient whereas in another patient Co-029 labelling was stronger on tumor (F) than on non tumorous colon epithelium (E). (scale bar, 20 μm).

Figure 5:
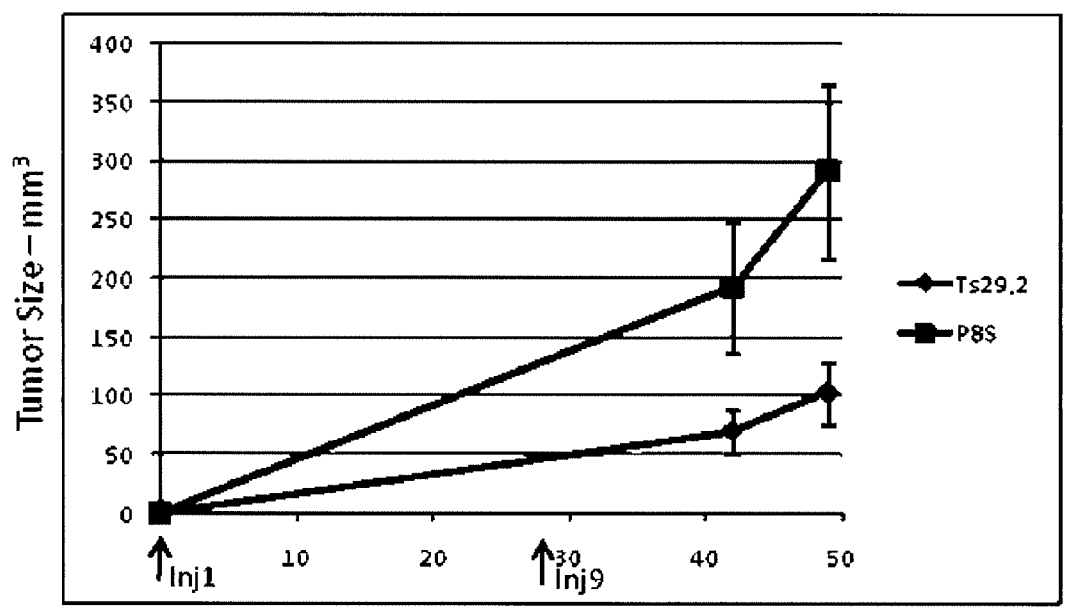

FIG. 5. Effect of antiCo-029 antibodies on subcutaneous tumor growth.

Measurements were made at J43 and J50. The monoclonal antibody Ts29.2 inhibits significantly the growth of Is1-Co029 cells with is a significant difference of tumor size between the two groups, antibody treated and PBS control, with a T/C % of 36% and 35% respectively (mean size at day 50: 195.7±47.7 vs 557±141.6 mm$^3$).

EXAMPLE

Material & Methods

Cells and Cell Culture.

The cell lines Isreco1, Isreco2 and Isreco3 were initially derived from a primary human colon cancer surgical specimen (Isreco1)(Duke's C, class III) and its corresponding liver and peritoneal metastases (Cajot et al., 1997). These cells were cultured in Dulbecco's modified Eagle's medium (DMEM) supplemented with 10% FCS, glutamax and antibiotics (all from Invitrogen). For experiments, tissue culture plastics were coated with rat tail Collagen I (BD Biosciences) for 1 hour at 50 μg/ml and rinsed with PBS.

Construction of the Co-029 and CD81 Lentiviral Vector and Transduction of Isreco1 Cells.

Since Isreco1 cells were not efficiently transfected by using non retroviral methods we constructed the TRIPΔ3-EF1α-Co029 and TRIPΔ3-EF1α-CD81 plasmids by inserting the human Co029 and the human CD81 cDNA coding sequence in TRIPΔ3-EF1α vectors. Vector particles were produced by transient calcium phosphate cotransfection of 293T cells by the TRIPΔ3-EF1α-CD81 and TRIPΔ3-EF1α-Co029 plasmids, an encapsidation plasmid and a vesicular stomatitis virus envelope expression plasmid, as described. Is1-Co029 and Is1-CD81 cells were obtained by transducing Isreco1 cells twice with concentrated lentiviral particles. Is1-Co029low cells were obtained following a single transduction.

Immunofluorescence.

For flow cytometry analysis of cell surface molecules, cells were detached using a non-enzymatic solution (Invitrogen), washed and stained with 10 m/ml of primary antibody. After washes in culture medium, cells were incubated with 10 μg/ml-1 FITC-labelled secondary antibody (Beckman Coulter), washed again three times and fixed with 1% formaldehyde in PBS. All incubations were performed for 30 min at 4° C. Analysis of cell-surface staining was performed using a FACScalibur flow cytometer (Becton-Dickinson, San Jose, Calif., USA).

For intracellular cytometry, cells were detached using trypsin or scrapped in PBS (4° C.) then fixed for 20 min at 4° C. with 1% formaldehyde in PBS. After centrifugation, cells were incubated in methanol 100% for 10 min at −20° C. then washed in PBS and stained with 10 μg/ml of primary antibody. After washes in PBS, cells were incubated with 10 μg ml FITC-labelled secondary antibody (Beckman Coulter), washed again three times and immediately analysed.

For in-situ labelling, cells cultured in labtek chambers were immunostained by fixing with 4% formaldehyde for 10 min followed by permeabilization with Triton X100 at 1% for 10 min. Incubation were performed in the chambers with first antibodies at 10 μs/ml followed by appropriate fluorochrome coupled 2nd antibodies at same concentration. For α2β1 integrin labelling, the fixation and permeabilization step was performed after incubation with the mAb Gi9 since the epitope didn't resist to the fixation procedure.

Antibodies.

Most anti-tetraspanin mAbs used in this study were produced in our laboratory Alb6 and TS9 (CD9), TS29 (Co-029/tspan8) and TS81(CD81). AZM22 (Co-029) was a gift of F. Lanza. The following commercial antibodies were purchased: mAb anti-Vinculin clone hVIN-1 (Sigma), mAb anti-integrin α1 (5E8D9, Sigma), mAb anti-integrin α2 Gi9 (Beckman Coulter Immunotech), mAb anti-integrin β1 4B4 (Beckman Coulter), mAb anti-E-Cadherin Hecd1 (Takara), mAb anti-E-cadherin 67A4 (Beckman Coulter), mAb anti-β-catenin, rabbit polyclonal anti-phospho-β-catenin (S33-37), goat polyclonal biotin-labeled anti-E-Cadherin (R§D System) and mAb anti-p120-catenin (clone 98, BD Transductions Laboratories). These antibodies were used as primary antibodies for immunoblotting, immunoprecipitation, immunostaining. F-actin was stained with Alexa Fluor 488 Phalloidin (Molecular Probes). Anti-integrin al 5E8D9, α2 Gi9, β1 4B4 and tetraspanin mAbs ALB6, TS29 and TS81 were also used for functional studies. For signalling molecules the following antibodies were used for intracellular flow cytometry: rabbit polyclonal anti-Phospho-p44/42 MAPK (Thr202, Tyr204), anti-Phospho-p38 MAPK (Thr180,Tyr182), anti-Phospho-SAPK/JNK (Thr183, Tyr185) (Cell signalling). F-actin was stained with Alexa 488 phalloidin (Molecular Probes).

For the production of TS29, that was not reported before, BALB/c mice were injected intraperitoneally twice with a mixture of 107 Isreco3 and Lovo cells and a final boost was performed 3 weeks later with CD9-containing complexes collected by immunoprecipitation from a Brij 97 lysate of 109 of Isreco3 cells. Spleen cells were fused with P3X63AG8 mouse myeloma cells (5×107 and 3×107 cells respectively) according to standard techniques and distributed into 96-well tissue culture plates. After two weeks hybridoma culture supernatants were harvested and tested for Isreco1 and Is1-Co029 staining by indirect immunofluorescence and analyzed using a microplate fluorescence reader (cytofluor II, Perseptive Biosystems, MA) and a flow cytometer. Positive supernatants were then further characterized by immunoprecipitation and by comparison with the Co-029 mAb AZM22.

Immunoprecipitation and crosslinking. Cells were lysed directly in the tissue culture flask (2 ml for a 150-cm2 flask) in lysis buffer (10 mM Tris (pH 7.4), 150 mM NaCl, 0.02% NaN3, 1 mM phenylmethylsulfonyl fluoride, 0.5 mg/ml leupeptin, 1 mg/ml pepstatin A and 10 kallikrein-inactivating units/ml aprotinin) containing 1% Triton X-100 (Roche Molecular Biochemicals, Meylan, France). After a 30-min incubation at 4° C., the insoluble material was removed by centrifugation at 10,000 g and the cell lysate was precleared overnight by addition of 0.005 volume of heat-inactivated goat serum and 0.025 volume of protein G-Sepharose beads (Amersham Pharmacia Biotech). Proteins were then immunoprecipitated by adding 2 μg/ml of antibodies and 30 μl of protein G-Sepharose beads to 1 ml of the lysate. After a 2-h incubation at 4° C. under constant agitation, the beads were washed five times in lysis buffer. The immunoprecipitates were separated by 5-15% SDS-polyacrylamide gel electrophoresis under nonreducing conditions and transferred to a Nitrocellulose membrane (Amersham Pharmacia Biotech). Western blotting on immunoprecipitates was performed using biotinylated mAbs and a Alexa Fluor 680-labelled streptavidin (Invitrogen) which was revealed with the Odyssey Infrared Imaging System (LI-COR Biosciences). For cross-linking, the cells were incubated for 30 min at 4° C. in the culture flask with 0.5 mM of water soluble BS3 (Pierce, Rockford, Ill.) in PBS 1×. They were washed three times in PBS 1× before lysis in 1% Triton X-100 at 4° C. and immunoprecipitation.

RNA Silencing.

Cells (1-3×105 cells in DMEM medium) were reverse transfected with synthetic si-RNA oligonucleotides using Interferrin (Ozyme) according to manufacturer's protocol.

6, 12 or 24 well cell culture plates were coated with rat tail collagen I. Plates were rinsed in PBS. One μl of the siRNA (10 μM) oligonucleotide mix was added to 96 μl. DMEM without serum and 3-5 μl Interferrin and incubated at room temperature in each well during 20 min to allow formation of transfection complexes. Cells detached by trypsin-EDTA were layered at appropriate concentration in 400 μl DMEM medium with serum (the final concentration of si-RNA was 20 nM).

Sequences of si-RNA were either obtained from the literature or chosen according to reported criteria. Only sequences allowing inhibition of at least 75% protein expression in our system were retained for the study and are listed below. The following si-RNA were synthetized by Eurogentec unless specified.

The si-RNA labelled with an asterisk were used throughout the study, the other si-RNA served as controls for specificity of the biological effects.

```
                                              (SEQ ID NO: 9)
*si CD53   GGAAAACAAGUGUCUGCUUdTdT (SEQ ID NO: 10)
*si-Co029  GGUAUCCUAGGAGCUGUUUdTdT (SEQ ID NO: 11)
*si-ECad1  GGGUUAAGCACAACAGCAAdTdT (Hayashida et al., 2005)

(SEQ ID NO: 12)
si-ECad2   CAGACAAAGACCAGGACUAdTdT (Hayashida et al., 2005)

(SEQ ID NO: 13)
si-ECad3   GAGUGAAUUUUGAAGAUUGdTdT (SEQ ID NO: 14)
si-ECad4   GCACGUACACAGCCCUAAUdTdT (si-ECad3 and si-ECad4 sequences were communicated by R Assoian)

(SEQ ID NO: 15)
si-VLA2-952D   ACGCCCUUGAUACUAAAAAdTdT (SEQ ID NO: 16)
*si-VLA2-994D  UCGCUAGUAUUCCAACAGAdTdT (SEQ ID NO: 17)
si-VLA1-280D   AGUUGGAUCUACCAGUUAAdTdT (SEQ ID NO: 18)
si-VLA1-171D   GAAGGAAAAUGGGUGCUUAdTdT (SEQ ID NO: 19)
si-VLA1-1286D  UGAACCGCUUGCUUCUUAUdTdT
```

-continued

*si-p120a GCCAGAGGUGGUUCGGAUAdTdT (SEQ ID NO: 20)

(Hou et al., 2006)

si-p120b gaugguuauccagguggcadTdT (SEQ ID NO: 21)

(Boguslavsky et al., 2007)

*si-Akt UGCCCUUCUACAACCAGGAdTdT (SEQ ID NO: 22)

(Katome et al., 2003)

*si-RhoA-02 GAACUAUGUGGCAGAUAUCdTdT (SEQ ID NO: 23) (Dharmacon)

*si-RhoC-03 GGAUCAGUGCCUUUGGCUAdTdT (SEQ ID NO: 24) (Dharmacon)

Three stealth si-RNA for Co-029 were also purchased from Invitrogen (Carlsbad, Calif.)

si-Co029s330 GCUCCUACGUUGCUGUGGACAUAUU (SEQ ID NO: 25)

si-Co029s789 CCUGAAUUAUGUGCCUGUCUAGAUA (SEQ ID NO: 26)

si-Co029s868 CCUGUAUUGCCAGAUCGGGAACAAA (SEQ ID NO: 27)

Videomicroscopy.

Analysis of 2D cell motility on collagen I films was performed using phase contrast on an inverted microscope (Axiovert 200; Zeiss, Oberkochen, Germany) equipped with an environmental chamber with 5% CO2 in air at 37° C. The microscope was driven by the Metamorph software (Roper Scientific), and images were recorded with a Coolsnap HQ camera (Roper Scientific). Stacks of phase contrast images were collected every 15 min for 24 h at ×200 magnification. Cell migration was quantified using the manual tracking plugin of ImageJ (Rasband, 2007) Raw data were transferred to Excel for speed calculations and statistical analysis was performed by the non parametric Mann-Whitney test in Graphpad. For each position at least 10 cells were analyzed. Experiments were repeated from 2 to 10 times to verify the robustness of the results and the stability of the measurements.

For silencing experiments, motility measures were performed 48 hours after RNAi treatments. The following inhibitors were used in motility experiments, U0126 (Promega) at 10 μM for the MAPK Erk, SB203580 (Calbiochem) at 20 nM for the MAPK p38, D-JNKI-1 (a gift of Xigen SA) at 3 μM with an overnight preincubation for JNK, LY294002 (Promega) at 20 μM for PI3K, the exotransferase C3 at 100 μg/ml with an overnight preincubation for inhibition of Rho (a gift of E. Lemichez), Akt was inhibited by RNAi.

Immunohistochemistry.

Antibody labelling was performed on tumor tissues from fifty two patients diagnosed and operated in 2002-3 at Hopital Europeen Georges Pompidou. These patients had not received treatment before surgical removal of the tumor and at least 12 lymph nodes were removed during surgery for correct assessment of tumor stage. Formalin-fixed, paraffin embedded tissue blocks containing carcinoma specimens were retrieved from the archives of the Department of Pathology. Blocks displaying simultaneously normal mucosal areas and carcinoma were identified on corresponding H&E-stained slide. Each paraffin section was placed on a positively charged glass slide (Superfrost). Slides containing the tissue section were baked for at least 24 hours in a 70° C.±5° C. oven. The slides were deparaffinized with xylene and transferred through changes of ethanol. The iVIEW™ DAB Detection Kit (Ventana Medical Systems) was used according to manufacturer instructions. For E-cadherin and p120ctn antigen retrieval was done by heating the slides at 98° C. for 30 min in a sodium citrate buffer (pH 9.0) and cooling for 15 min. Slides used for CD9 and Co-029 labelling were treated with protease for 4 min at 37° C. for antigen retrieval. The following steps were performed using a BenchMark XT Automated Slide Stainer. Concentrations of primary antibodies were as follows E-cadherin 2.5 μg/ml, p120ctn 2 μg/ml, CD9 (TS9) and Co-029 (TS29) 1 μg/ml. The labelling was visualized with diaminobenzidine and counterstained with hematoxylin, dehydrated, transferred to a xylene bath and mounted with Permount (Sigma). Each section was analyzed for protein localization (junctional or cytoplasmic p120-ctn and E-cadherin) and intensity of staining and was scored by eye as −1, 0, +1 by comparing labelling of normal mucosa and tumor (low expression means that the tumor is less labelled than normal epithelium, whereas expression is considered as strong when it is at least equal to normal epithelium). Fisher's exact test and Chi square test were applied for statistical analysis using Graphpad software.

Effect of antiCo-029 Antibodies on Subcutaneous Tumor Growth.

In order to realize the animal experiments, a large amounts of purified mAbs was prepared. The yield of mAb TS29.2 (IgG2b) was of approximately 5 mg purified mAb/ml ascitis. Mice produce a mean of 10 ml ascitis/mouse.

Ascitis were clarified by centrifugation and 0.45 μm filtered. The mAbs were purified by using the Biosepra MEP HyperCel* Hydrophobic Charge Induction Chromatography (HCIC) Sorbent, dialysed against PBS and the purity checked by gel electrophoresis and Coomassie Blue coloration. Fractions were aliquoted and frozen at −20° C.

The effect of the antibodies on tumor growth was evaluated by subcutaneous implantation of tumor cells issued from colon carcinoma cell lines, followed by repeated injections of monoclonal antibodies with appropriate controls.

Ten Nude mice were injected subcutaneously with $10^7$ Is1-Co029 tumor cells and divided in two groups, antibody treated and PBS control. Each group received an i.p. injection of either 1 mg Ts29.2 or the same volume of PBS and biweekly subsequent injections of 1 mg Ts29.2 or PBS i.p., for a total of nine injections. The size of the tumor was determined by the formula (π/6×length×width×thickness).

Tumor growth inhibition (T/C %) was defined as the ratio of the median tumor volume for the treated vs. control group. It will be calculated as T/C %=[(median tumor volume of treated group at day X)/(median tumor volume of control group at day X)]×100.

Results Some of the results reported below were presented in a scientific article (Greco C. et al., 2010).

Generation of Isreco1 Colon Carcinoma Cell Lines Expressing Co-029.

For functional studies, the Co-029 negative Isreco1 cells were transduced with lentiviral vectors in order to obtain an expression of Co-029 similar to the metastatic cell line Isreco2 (Supplementary FIG. 1). Two Co-029 expressing Isreco1 cell lines were used: Is1-Co029 (with a high expression of Co-029) and Is1-Co029low. Isreco1 and Is1-CD81 (transduced with the tetraspanin CD81) were used as controls.

Relation Between E-Cadherin and Co-029 in Cell Motility.

We explored by videomicroscopy whether cell motility could be altered by the forced expression of Co-029. As Isreco1 cells don't move on tissue culture plastic, we tested different matrices (matrigel, laminin 5, collagen I). The cells migrate randomly with the highest velocity on collagen I that was retained for the rest of the study. Sparse Isreco cells are intensely motile through cell-matrix interactions since the blocking mAb anti β1 integrin chain 4B4, that inhibits the collagen I receptors α1β1 and α2β1 (White et al., 2004), completely stopped the cells. On collagen I, Isreco1 and Is1-Co029 sparse cells formed focal adhesions containing vinculin, paxillin and Fak with anchored actin fibers. The integrin α2β1 clustered at focal adhesions whereas α1β1 expression was punctuated and diffuse.

Migration is arrested when cell density increases favoring cell contacts that are stabilized by the formation of adherens junctions but surprisingly, E-cadherin was well expressed on motile sparse cells (FIG. 1A) with a diffuse membrane distribution raising the question of a possible role of free E-cadherin in cell motility. Whereas velocity of Isreco1 and Is1-Co029 sparse cells wasn't significantly different, silencing of E-cadherin effectively increased the motility of Is1-Co029 cells (FIG. 1B), an effect confirmed with 4 different small interfering RNA (si-RNA). The specific role of Co-029 in the effect of E-cadherin RNAi was demonstrated by the facts that (i) it was reversed by Co-029 RNAi (FIG. 1B) with 4 different si-RNA, (ii) it was not observed with the parental line Isreco1, (iii) Co-029 silencing had no effect on basal Is1-Co029 cells without E-cadherin knock-down. Altogether, this confirms that, when Co-029 is expressed, E-cadherin has an inhibitory effect on cell migration of sparse cells. Interestingly, we observed a colocalization of E-cadherin and Co-029 at cell junctions (FIG. 1C) and their physical association is suggested by chemical cross-linking (FIG. 1D).

p120ctn Silencing Induces a Co-029 Dependent Cell Motility Acceleration.

Figure 2A:
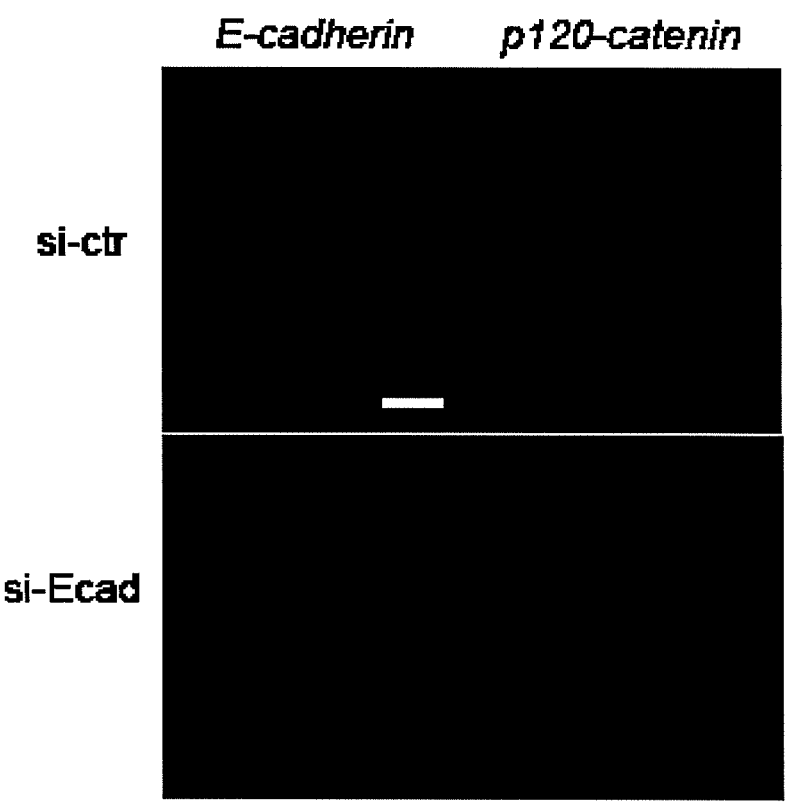
Figure 2B:
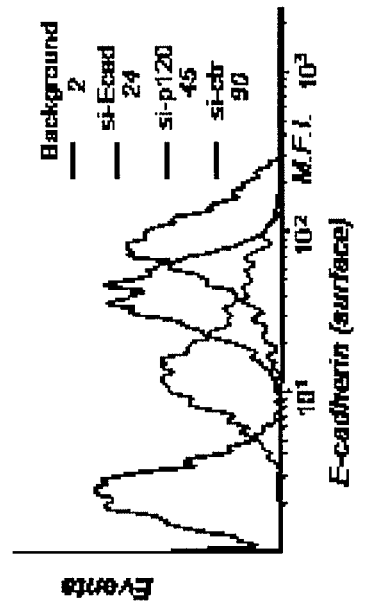
Figure 2C:
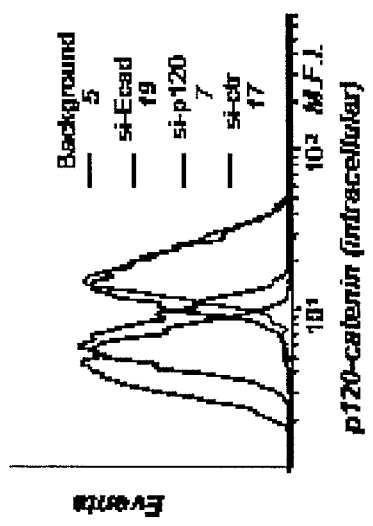
Figure 2D:
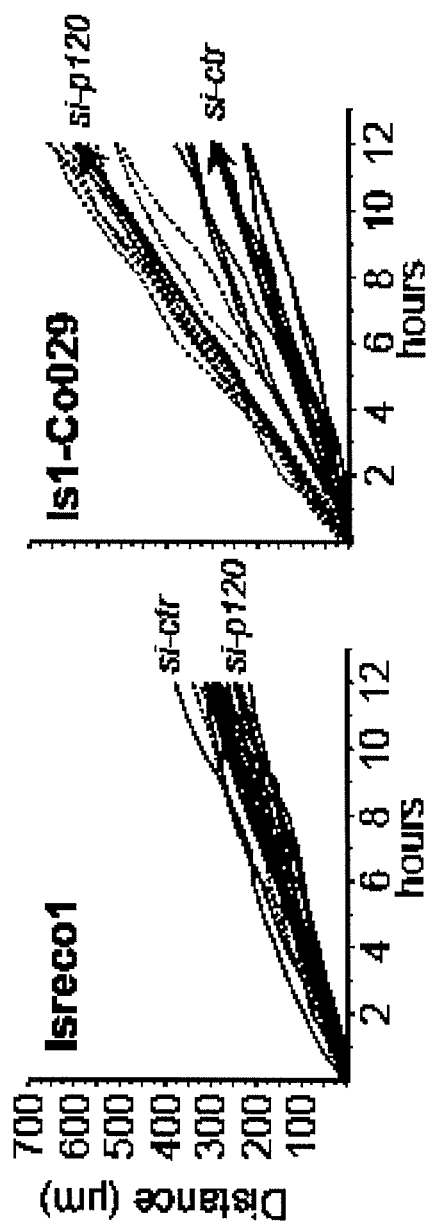
Figure 2E:
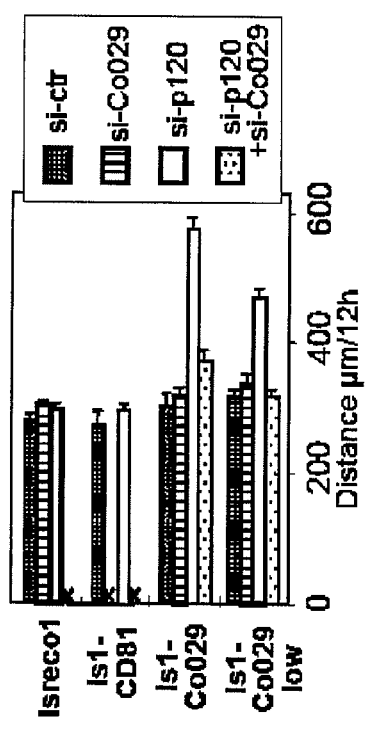

A possible link between Co-029, E-cadherin and motility could be the signalling molecule p120ctn that is retained at cell membrane through its affinity for E-cadherin (Anastasiadis, 2007; Reynolds and Roczniak-Ferguson, 2004; McCrea and Park, 2007; Xiao et al., 2007) and has been reported to regulate Rho and Rac functions in cell adhesion and motility (Anastasiadis et al., 2000; Noren et al., 2000). Upon E-cadherin RNAi a major part of p120ctn relocalized to the nucleo-cytoplasmic area in Isreco1 and Is1-Co029 cells (FIG. 2A). Flow cytometry analysis of permeabilized cells after E-cadherin RNAi shows that there is no change in total cellular content of p120ctn (FIG. 2B), confirming the absence of rapid degradation of cytoplasmic p120ctn reported earlier (Thoreson et al., 2000). The role of p120ctn in mediating E-cadherin effects on cell migration was explored using RNAi. The level of p120ctn was reduced by 85% after silencing and was accompanied by a 50% decrease in E-cadherin surface expression (FIG. 2C), consistent with the ability of p120ctn to stabilize E-cadherin at the cell surface (Davis et al., 2003; Xiao et al., 2007). The silencing of p120ctn dramatically increased the motility of Is1-Co029 cells by nearly 80% (FIG. 2D-E). The same effect was obtained with two different si-RNA. Again the effect of p120ctn silencing on motility was clearly linked to the presence of Co-029 since (i) it was not observed after simultaneous p120ctn and Co-029 silencing (FIG. 2E) as confirmed with 4 different si-RNA to Co-029; (ii) Is1-Co029 low cells were less accelerated by p120ctn silencing than Is1-Co029 cells; (iii) neither Isreco1 nor Is1-CD81 cells accelerated after p120ctn silencing. The effect of p120ctn silencing on cell migration is not a consequence of the reduced E-cadherin surface expression since this reduction is less pronounced than after E-cadherin silencing. On the contrary, these data are compatible with the hypothesis that p120ctn mediates the effect of E-cadherin on cell migration. The fact that both silencing and delocalization to the nucleo-cytoplasmic area (through E-cadherin silencing) produce the same effect suggests that in our model, the membrane bound p120ctn can deliver a negative signal for the migration process.

To check that the effect of p120ctn silencing on cell migration was not an artefact of the Is1-Co029 transduced cells, we derived from the Co-029 positive metastatic cell line Isreco2, that grows as tight cellular aggregates, cell clones in which cells grow separately allowing migration analysis of independent cells. These new cell lines that express strongly Co-029 were migrating more slowly than Isreco1 or Is1-Co029 cells but as for Is1-Co029 their velocity was strongly increased by p120ctn silencing.

We also performed transwell experiments in which cells had to migrate through collagen coated membranes. Results showed that p120ctn silencing provided an advantage for both cell lines but that it was slightly significantly superior for Is1-Co029 cells.

Cell Signalling in p120ctn Silenced Cells—Role of Small G Proteins.

Figure 2F:
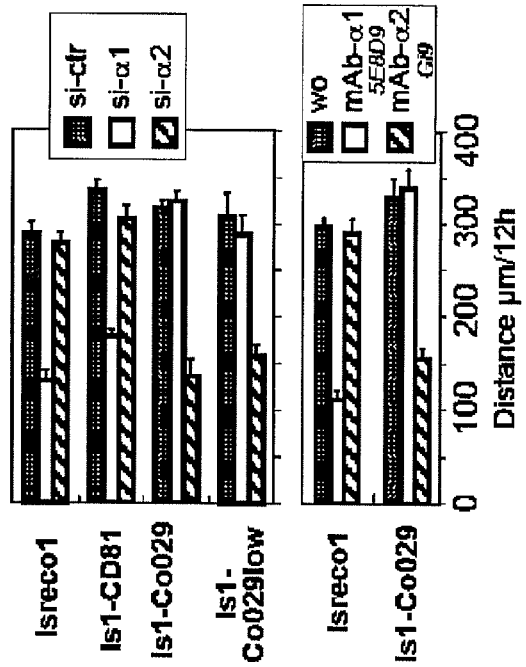
Figure 2G:
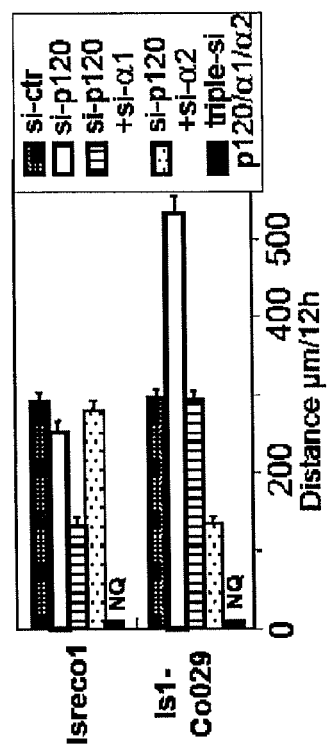

We then searched the mechanisms mediating acceleration of Is1-Co029 cells upon p120ctn silencing by analyzing the contribution of α1β1 and α2β1 integrins in the motility process. It was firstly observed using RNAi and function blocking antibodies that whereas Isreco1 and Is1-CD81 cell motility relied preferentially on al 131 integrin, the motility of Is1-Co029 cells relied mainly on α2β1 integrin (FIG. 2F). This observation shows that upon expression of Co-029, signalling from the α2β1 integrin receptor is recruited. Furthermore, we observed that the p120ctn silencing acts also on integrin signalling since the increased velocity of Is1-Co029 required signalling from both α1β1 and α2β1 integrins as demonstrated by RNAi (FIG. 2G).

We investigated then the pathways reported to be involved in cell motility following integrin stimulation (Guo and Giancotti, 2004). Inhibitors of the mitogen-activated protein kinase pathways Erk1/2, p38-MAPK and JNK reduced the motility of Is1-Co029 cells particularly after p120ctn silencing (FIG. 3A). However the effect on Isreco1 was marginal or absent. The same results were obtained by Akt1-2 silencing. The complete blockade of motility by LY294002 showed that, in this system, motility is highly dependent on PI3K perhaps due to spatial patterns of 3'PI lipid products at the membrane that control the optimal localization of signalling molecules. Treatment with C3 exotransferase, that inhibits Rho-GTPases, or silencing of RhoA, but not RhoC, accelerated Is1-Co029 cells to the same extent as p120ctn silencing (the effects were not cumulative) indicating that RhoA inhibits motility of Is1-Co029 cells (FIG. 3B). On the other hand, C3 exotransferase and RhoA silencing slowed down Isreco1 cells suggesting that in these cells some RhoA signalling is necessary for full velocity. We also monitored by flow cytometry single cells events with phospho-specific antibodies for activated forms of signalling molecules (Krutzik and Nolan, 2003). Upon p120ctn silencing, there was a reproducible increase of piNK and pAkt in Is1-Co029 cells (FIG. 3C). Altogether, in Is1-Co029 cells, the potent effect of RhoA inhibition and the activation by si-p120 of JNK, that is downstream of Rac, support a role for small G proteins in the mechanisms triggered by Co-029 expression. Since the balance between Rac and RhoA is regulated by p120ctn, this suggests that p120ctn associated to surface E-cadherin could control the motility of Is1-Co029 cells, at least partially, through local regulation of small G-proteins. The requirement for a membrane location of N-cadherin associated p120ctn for regulation of Rho proteins was already reported (Wildenberg et al., 2006).

p120ctn Delocalization and Co-029 High Expression are Adverse Prognostic Factors in Human Colon Carcinoma.

These results led us to test the relation of Co-029 expression with prognosis by analyzing the primary tumors of 52 patients with colon carcinoma. We compared the results with p120ctn delocalization (FIG. 4 and Table B) that is related to aggressive disease (Bellovin et al., 2005). Conditions were optimized for antigenic revelation of Co-029 in formalin-fixed paraffin embedded tissues giving a labelling pattern identical to that found previously in frozen tissue sections (Le Naour et al., 2006). Since quantification of labelling is difficult on tissue sections, we took advantage of the expression of Co-029 on normal epithelial cells to use it as a reference for grading the tumor labelling. The comparison of labelling in normal epithelium and in tumor areas was performed on the same sections.

Of the 24 patients who died or relapsed in the 3 years following tumor removal, 71% (17/24) had p120ctn delocalization and 87% (21/24) had high Co-029 expression, whereas it was respectively 25% (7/28) (p=0.0019) and 57% (16/28) (p=0.029) for the patients group in complete remission at 3 years. The pattern of p120ctn expression was also significantly related to initial staging of the tumor whereas it was not significant for Co-029. The pattern of p120ctn expression was not significantly correlated to the level of Co-029 (p=0.269) indicating that these two markers may vary independently.

p120 Silencing Renders Cells Sensitive to a Motility Inhibitory Effect of Co-029 mAb.

In an attempt to target functional properties of tumor cell, we measured cell motility of cells exposed to antibodies. Co-029 mAb TS29 had a unique effect in provoking a 75% motility reduction of Is1-Co029 cells silenced for p120ctn, whereas no effect of mAbs to tetraspanins CD9, Co-029 and CD81 were noted on the different untreated cell lines. This indicates that in conditions where p120ctn expression is delocalized and Co-029 well expressed, as it happens frequently in pathological situations, motility of the cells could be significantly down-regulated.

TABLE B

Outcome and staging of 52 patients according to p120ctn localization and Co-029 expression in primary tumor. Correlations between p120ctn localization and Co-029 expression level and either evolution or staging of the 52 colon carcinoma patients analyzed for p120ctn localization and intensity of Co-029 expression in primary tumor. Cytoplasmic localization of p120ctn and high Co-029 expression are statistically significant adverse outcome factors (upper part of the table B). In the lower part of the table B, group 1 corresponds to patients without adverse prognosis factors according to p120ctn localization and Co-029 expression, group 2 includes patients with one adverse factor and group 3 patients have two adverse factors. The localization of p120ctn is linked to staging whereas the association isn't significant for Co-029 expression, n = number of patients, CR = Complete Remission, † = death, Rel = Relapse, mb = membrane, cyt = cytoplasm.

| | n | | Outcome at 3 years | | | Staging (WHO) | | |
|---|---|---|---|---|---|---|---|---|
| | | | CR (n = 28) | † (n = 20) Rel (n = 4) | | 1-3b (n = 27) | 3c-4 (n = 25) | |
| p120ctn membrane | 28 | | 21 | 7 | p = 0.0019 | 20 | 8 | p = 0.0049 |
| p120ctn cytoplasm | 24 | | 7 | 17 | | 7 | 17 | |
| Co-029 low | 15 | | 12 | 3 | p = 0.029 | 11 | 4 | p = 0.1238 |
| Co-029 high | 37 | | 16 | 21 | | 17 | 20 | |
| p120ctn mb Co-029 low | 12 | group 1 | 10 | 2 | p = 0.0012 | 9 | 3 | p = 0.0036 |
| p120ctn at Co-029 low | 3 | group 2 | 2 | 1 | | 2 | 1 | |
| p120ctn mb Co-029 high | 16 | | 11 | 5 | | 11 | 5 | |
| p120ctn cyt Co-029 high | 21 | group 3 | 5 | 16 | | 5 | 16 | |

Effect of antiCo-029 Antibodies on Subcutaneous Tumor Growth

Tumor outcome for both groups of mice is shown in FIG. 5. Measurements were made at day 43 and day 50. It appears that there is a significant difference of tumor size between the two groups with a T/C % of 36% and 35% respectively (mean size at day 50: 195.7±47.7 vs 557±141.6 mm$^3$). The monoclonal antibody Ts29.2 inhibits significantly the growth of Is1-Co029 cells.

REFERENCES

Throughout this application, various references describe the state of the art to which this invention pertains. The disclosures of these references are hereby incorporated by reference into the present disclosure.

Anastasiadis, P. Z. (2007). p120-ctn: A nexus for contextual signaling via Rho GTPases. Biochim Biophys. Acta 1773, 34-46.

Anastasiadis, P. Z., Moon, S. Y., Thoreson, M. A., Mariner, D. J., Crawford, H. C., Zheng, Y., and Reynolds, A. B. (2000). Inhibition of RhoA by p120 catenin. Nat. Cell Biol 2, 637-644.

Bellovin, D. I., Bates, R. C., Muzikansky, A., Rimm, D. L., and Mercurio, A. M.
(2005). Altered localization of p120 catenin during epithelial to mesenchymal transition of colon carcinoma is prognostic for aggressive disease. Cancer Res. 65, 10938-10945.

Boguslaysky, S., Grosheva, I., Landau, E., Shtutman, M., Cohen, M., Arnold, K., Feinstein, E., Geiger, B., and Bershadsky, A. (2007). p120 catenin regulates lamellipodial dynamics and cell adhesion in cooperation with cortactin. Proc. Natl. Acad. Sci. U. S. A 104, 10882-10887.

Boucheix, C. and Rubinstein, E. (2001). Tetraspanins. Cell Mol. Life Sci. 58, 1189-1205.

Brady G, Jantzen H M, Bernard H U, Brown R, Schutz G, Hashimoto-Gotoh T. New cosmid vectors developed for eukaryotic DNA cloning. Gene. 1984 February; 27(2): 223-32.

Brummelkamp T R, Bernards R, Agami R. A system for stable expression of short interfering RNAs in mammalian cells. Science. 2002 Apr. 19; 296(5567):550-3.

Cajot, J. F., Sordat, I., Silvestre, T., and Sordat, B. (1997). Differential display cloning identifies motility-related protein (MRP1/CD9) as highly expressed in primary compared to metastatic human colon carcinoma cells. Cancer Res. 57, 2593-2597.

Caron P C, Laird W, Co M S, Avdalovic N M, Queen C, Scheinberg D A. Engineered humanized dimeric forms of IgG are more effective antibodies. J Exp Med. 1992 Oct. 1; 176(4):1191-5.

Charrin, S., Le Naour, F., Silvie, O., Milhiet, P. E., Boucheix, C., and Rubinstein, E. (2009). Lateral organization of membrane proteins: tetraspanins spin their web. Biochem. J. 420, 133-154.

Claas C, Seiter S, Claas A, Savelyeva L, Schwab M, Zoller M. Association between the rat homologue of CO-029, a metastasis-associated tetraspanin molecule and consumption coagulopathy. J Cell Biol. 1998; 141(1):267-80.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Davis, M. A., Ireton, R. C., and Reynolds, A. B. (2003). A core function for p120-catenin in cadherin turnover. J Cell Biol 163, 525-534.

Edge A S, Faltynek C R, Hof L, Reichert L E Jr, Weber P. Deglycosylation of glycoproteins by trifluoromethanesulfonic acid. Anal Biochem. 1981 Nov. 15; 118(1):131-7.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.

Greco C, Bralet M P, Ailane N, Dubart-Kupperschmitt A, Rubinstein E, Le Naour F, Boucheix C. E-cadherin/p120-catenin and tetraspanin Co-029 cooperate for cell motility control in human colon carcinoma. Cancer Res. 2010; 70(19):7674-83.

Guo, W. and Giancotti, F. G. (2004). Integrin signalling during tumour progression. Nat. Rev. Mol. Cell Biol. 5, 816-826.

Hannon G J. RNA interference. Nature. 2002 Jul. 11; 418(6894):244-51.

Hayashida, Y., Honda, K., Idogawa, M., Ino, Y., Ono, M., Tsuchida, A., Aoki, T., Hirohashi, S., and Yamada, T. (2005). E-cadherin regulates the association between beta-catenin and actinin-4. Cancer Res. 65, 8836-8845.

Hou, J. C., Shigematsu, S., Crawford, H. C., Anastasiadis, P. Z., and Pessin, J. E. (2006). Dual regulation of Rho and Rac by p120 catenin controls adipocyte plasma membrane trafficking. J Biol Chem. 281, 23307-23312.

Jayasena S. D. (1999) Aptamers: an emerging class of molecules that rival antibodies in diagnostics. Clin Chem. 45(9):1628-50.

Kanetaka, K. et al. Possible involvement of tetraspanin CO-029 in hematogenous intrahepatic metastasis of liver cancer cells. J Gastroenterol. Hepatol. 2003; 18: 1309-14.

Katome, T., Obata, T., Matsushima, R., Masuyama, N., Cantley, L. C., Gotoh, Y., Kishi, K., Shiota, H., and Ebina, Y. (2003). Use of RNA interference-mediated gene silencing and adenoviral overexpression to elucidate the roles of AKT/protein kinase B isoforms in insulin actions. J Biol Chem. 278, 28312-28323.

Kohler G, Milstein C. Continuous cultures of fused cells secreting antibody of predefined specificity. Nature. 1975 Aug. 7; 256(5517):495-7.

Krutzik, P. O. and Nolan, G. P. (2003). Intracellular phospho-protein staining techniques for flow cytometry: monitoring single cell signaling events. Cytometry A 55, 61-70.

Kuwana Y, Asakura Y, Utsunomiya N, Nakanishi M, Arata Y, Itoh S, Nagase F,
Kurosawa Y. Expression of chimeric receptor composed of immunoglobulin-derived V regions and T-cell receptor-derived C regions. Biochem Biophys Res Commun. 1987 Dec. 31; 149(3):960-8.

Le Naour F, André M, Greco C, Billard M, Sordat B, Emile J F, Lanza F, Boucheix C, Rubinstein E. Profiling of the tetraspanin web of human colon cancer cells. Mol Cell Proteomics. 2006 May; 5(5):845-57. Epub 2006 Feb. 7.

Mason J O, Williams G T, Neuberger M S. Transcription cell type specificity is conferred by an immunoglobulin VH gene promoter that includes a functional consensus sequence. Cell. 1985 June; 41(2):479-87.

McCrea, P. D. and Park, J. I. (2007). Developmental functions of the P120-catenin sub-family. Biochim Biophys. Acta 1773, 17-33.

McManus M T, Sharp P A. Gene silencing in mammals by small interfering RNAs. Nat Rev Genet. 2002 October; 3(10):737-47.

Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.

Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.

Padlan E A. A possible procedure for reducing the immunogenicity of antibody variable domains while preserving their ligand-binding properties. Mol Immunol. 1991 April-May; 28(4-5):489-98.

Rasband, W. S. ImageJ, U. S. National Institutes of Health, Bethesda, Md., USA. rsb.info.nih.gov/ij/. 2007

Reynolds, A. B. and Roczniak-Ferguson, A. (2004). Emerging roles for p120-catenin in cell adhesion and cancer. Oncogene 23, 7947-7956.

Riechmann L, Clark M, Waldmann H, Winter G Reshaping human antibodies for therapy. Nature. 1988 Mar. 24; 332(6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Sela, B. A., Steplewski, Z., and Koprowski, H. Colon carcinoma-associated glycoproteins recognized by monoclonal antibodies CO-029 and GA22-2. Hybridoma. 1989; 8, 481-491.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Shopes B. A genetically engineered human IgG mutant with enhanced cytolytic activity. J Immunol. 1992 May 1; 148(9):2918-22.

Sojar H T, Bahl O P. A chemical method for the deglycosylation of proteins. Arch Biochem Biophys. 1987 Nov. 15; 259(1):52-7.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Thoreson, M. A., Anastasiadis, P. Z., Daniel, J. M., Ireton, R. C., Wheelock, M. J., Johnson, K. R., Hummingbird, D. K., and Reynolds, A. B. (2000). Selective uncoupling of p120(ctn) from E-cadherin disrupts strong adhesion. J Cell Biol 148, 189-202.

Thotakura N R, Bahl O P. Enzymatic deglycosylation of glycoproteins. Methods Enzymol. 1987; 138:350-9.

Tuerk C. and Gold L. (1990) Systematic evolution of ligands by exponential enrichment: RNA ligands to bacteriophage T4 DNA polymerase. Science. 3; 249(4968):505-10.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Urlaub G, Chasin L A. Isolation of Chinese hamster cell mutants deficient in dihydrofolate reductase activity. Proc Natl Acad Sci USA. 1980 July; 77(7):4216-20.

White, D. J., Puranen, S., Johnson, M. S., and Heino, J. (2004). The collagen receptor subfamily of the integrins. Int. J Biochem. Cell Biol 36, 1405-1410.

Wildenberg, G. A., Dohn, M. R., Carnahan, R. H., Davis, M. A., Lobdell, N. A., Settleman, J., and Reynolds, A. B. (2006). p120-catenin and p190RhoGAP regulate cell-cell adhesion by coordinating antagonism between Rac and Rho. Cell 127, 1027-1039.

Xiao, K., Oas, R. G., Chiasson, C. M., and Kowalczyk, A. P. (2007). Role of p120-catenin in cadherin trafficking. Biochim. Biophys. Acta 1773, 8-16.

Zhou, Z., Ran, Y. L., Hu, H., Pan, J., Li, Z. F., Chen, L. Z., Sun, L. C., Peng, L., Zhao, X. L., Yu, L., Sun, L. X., and Yang, Z. H. TM4SF3 promotes esophageal carcinoma metastasis via upregulating ADAM12m expression. Clin. Exp. Metastasis. 2008; 25, 537-548.

Zöller, M. (2009) Tetraspanins: push and pull in suppressing and promoting metastasis. Nat.Rev.Cancer 9:40-55.

---

The invention claimed is:

1. A method of treating a Co-029-expressing cancer in a patient in need thereof, comprising administering to said patient a therapeutically effective amount of a Co-029 antibody directed against human Co-029, wherein the Co-029 antibody comprises the six complementarity determining region (CDR) sequences of an antibody which is obtainable from the hybridoma accessible under CNCM deposit number I-4046 or the six complementarity determining region (CDR) sequences of an antibody which is obtainable from the hybridoma accessible under CNCM deposit number I-4047.

2. The method of claim 1, wherein said Co-029 antibody is obtainable from the hybridoma accessible under CNCM deposit number I-4046 or I-4047.

3. A method for inhibiting the migration of cancer cells which express Co-029, comprising, exposing said cancer cells to an antibody directed against human Co-029, wherein the Co-029 antibody comprises the six complementarity determining region (CDR) sequences of an antibody which is obtainable from the hybridoma accessible under CNCM deposit number I-4046 or the six complementarity determining region (CDR) sequences of an antibody which is obtainable from the hybridoma accessible under CNCM deposit number I-4047.

4. The method of claim 1, wherein said Co-029 antibody is obtainable from the hybridoma accessible under CNCM deposit number I-4046 or I-4047.

5. The method of claim 1, wherein the Co-029 antibody comprises the variable light (VL) chain and the variable heavy (VH) chain of an antibody which is obtainable from the hybridoma accessible under CNCM deposit number I-4046 or the variable light (VL) chain and the variable heavy (VH) chain of an antibody which is obtainable from the hybridoma accessible under CNCM deposit number I-4047.

6. The method of claim 1, wherein the Co-029 antibody is a humanized antibody.

7. The method of claim 1, wherein the six CDR sequences of the Co-029 antibody comprise SEQ ID NO:2 for H-CDR1, SEQ ID NO:3 for H-CDR2, SEQ ID NO:4 for H-CDR3, SEQ ID NO:6 for L-CDR1, SEQ ID NO:7 for L-CDR2 and SEQ ID NO:8 for L-CDR3.

8. The method of claim 7, wherein the Co-029 antibody comprises a variable heavy (VH) chain region having the amino acid sequence set forth as SEQ ID NO: 1 and a variable light (VL) chain region having the amino acid sequence set forth as SEQ ID NO: 5.

9. The method of claim 3, wherein the Co-029 antibody comprises the variable light (VL) chain and the variable heavy (VH) chain of an antibody which is obtainable from the hybridoma accessible under CNCM deposit number I-4046 or the variable light (VL) chain and the variable heavy (VH) chain of an antibody which is obtainable from the hybridoma accessible under CNCM deposit number I-4047.

10. The method of claim 3, wherein the Co-029 antibody is a humanized antibody.

11. The method of claim 3, wherein the six CDR sequences of the Co-029 antibody comprise SEQ ID NO:2 for H-CDR1, SEQ ID NO:3 for H-CDR2, SEQ ID NO:4 for H-CDR3, SEQ ID NO:6 for L-CDR1, SEQ ID NO:7 for L-CDR2 and SEQ ID NO:8 for L-CDR3.

12. The method of claim 11, wherein the Co-029 antibody comprises a variable heavy (VH) chain region having the amino acid sequence set forth as SEQ ID NO: 1 and a variable light (VL) chain region having the amino acid sequence set forth as SEQ ID NO: 5.

* * * * *

SEQUENCE LISTING

```
<160> NUMBER OF SEQ ID NOS: 27

<210> SEQ ID NO 1
<211> LENGTH: 121
<212> TYPE: PRT
<213> ORGANISM: Artificial Sequence
<220> FEATURE:
<223> OTHER INFORMATION: Synthetic VH

<400> SEQUENCE: 1

Glu Val Lys Val Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Arg Val Ser Gly Tyr Thr Thr Glu Tyr Ser Ala
    50                  55                  60

Ser Val Gln Gly Arg Phe Thr Ile Ser Arg Asp Asn Ser Gln Ser Ile
65                  70                  75                  80
```

```
Leu Tyr Leu Gln Met Asn Thr Leu Arg Ala Glu Asp Ser Ala Thr Tyr
                85                  90                  95

Tyr Cys Ala Arg Asp His Tyr Gly Asn Phe Ala Met Asp Tyr Trp Gly
            100                 105                 110

Gln Gly Thr Ser Val Thr Val Ser Ser
            115                 120

<210> SEQ ID NO 2
<211> LENGTH: 8
<212> TYPE: PRT
<213> ORGANISM: Artificial Sequence
<220> FEATURE:
<223> OTHER INFORMATION: Synthetic H-CDR1

<400> SEQUENCE: 2

Gly Phe Thr Phe Thr Asp Tyr Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic H-CDR2

<400> SEQUENCE: 3

Ile Arg Asn Arg Val Ser Gly Tyr Thr Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic H-CDR3

<400> SEQUENCE: 4

Ala Arg Asp His Tyr Gly Asn Phe Ala Met Asp Tyr
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Synthetic VL

<400> SEQUENCE: 5

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Ser Tyr Tyr Cys Gln Gln Tyr Trp Ser Thr Pro Phe
                85                  90                  95

Thr Phe Gly Ser Gly Thr Lys Leu Glu Ile Lys
            100                 105
```

```
<210> SEQ ID NO 6
<211> LENGTH: 6
<212> TYPE: PRT
<213> ORGANISM: Artificial Sequence
<220> FEATURE:
<223> OTHER INFORMATION: Synthetic L-CDR1

<400> SEQUENCE: 6

Glu Asp Ile Tyr Asn Arg
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic L-CDR2

<400> SEQUENCE: 7

Gly Ala Thr
1

<210> SEQ ID NO 8
<211> LENGTH: 9
<212> TYPE: PRT
<213> ORGANISM: Artificial Sequence
<220> FEATURE:
<223> OTHER INFORMATION: Synthetic L-CDR3

<400> SEQUENCE: 8

Gln Gln Tyr Trp Ser Thr Pro Phe Thr
1               5

<210> SEQ ID NO 9
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 9
ggaaaacaag ugucugcuu                                            19

<210> SEQ ID NO 10
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 10 gguaccuag gagcuguuu                                             19

<210> SEQ ID NO 11
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 11
ggguuaagca caacagcaa                                            19

<210> SEQ ID NO 12
<211> LENGTH: 19
<212> TYPE: RNA
```

```
<213> ORGANISM: Artificial Sequence
<220> FEATURE:
<223> OTHER INFORMATION: Synthetic siRNA

<400> SEQUENCE: 12
cagacaaaga ccaggacua                                                  19

<210> SEQ ID NO 13
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 13
gagugaauuu ugaagauug                                                  19

<210> SEQ ID NO 14
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 14
gcacguacac agcccuaau                                                  19

<210> SEQ ID NO 15
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 15
acgcccuuga uacuaaaaa                                                  19

<210> SEQ ID NO 16
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 16
ucgcuaguau uccaacaga                                                  19

<210> SEQ ID NO 17
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 17
aguuggaucu accaguuaa                                                  19

<210> SEQ ID NO 18
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 18
gaaggaaaau gggugcuua                                                  19
```

<210> SEQ ID NO 19
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 19
ugaaccgcuu gcuucuuau                                              19

<210> SEQ ID NO 20
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 20
gccagaggug guucggaua                                              19

<210> SEQ ID NO 21
<211> LENGTH: 20
<212> TYPE: RNA
<213> ORGANISM: Artificial Sequence
<220> FEATURE:
<223> OTHER INFORMATION: Synthetic siRNA

<400> SEQUENCE: 21
gaugguuauc cagguggcad                                             20

<210> SEQ ID NO 22
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 22
ugcccuucua caaccagga                                              19

<210> SEQ ID NO 23
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 23
gaacuaugug gcagauauc                                              19

<210> SEQ ID NO 24
<211> LENGTH: 19
<212> TYPE: RNA
<213> ORGANISM: Artificial Sequence
<220> FEATURE:
<223> OTHER INFORMATION: Synthetic siRNA

<400> SEQUENCE: 24
ggaucagugc cuuuggcua                                              19

<210> SEQ ID NO 25
<211> LENGTH: 25
<212> TYPE: RNA
<213> ORGANISM: Artificial Sequence
<220> FEATURE:

```
<223> OTHER INFORMATION: Synthetic siRNA

<400> SEQUENCE: 25
gcuccuacgu ugcuguggac auauu                                              25

<210> SEQ ID NO 26
<211> LENGTH: 25
<212> TYPE: RNA
<213> ORGANISM: Artificial Sequence
<220> FEATURE:
<223> OTHER INFORMATION: Synthetic siRNA

<400> SEQUENCE: 26
ccugaauuau gugccugucu agaua                                              25

<210> SEQ ID NO 27
<211> LENGTH: 25
<212> TYPE: RNA
<213> ORGANISM: Artificial Sequence
<220> FEATURE:
<223> OTHER INFORMATION: Synthetic siRNA

<400> SEQUENCE: 27
ccuguauugc cagaucggga acaaa                                              25
```